United States Patent
Lindholm et al.

(10) Patent No.: US 7,026,029 B2
(45) Date of Patent: *Apr. 11, 2006

(54) REACTIVE MATERIALS FOR LIMITED PLAY OPTICAL DEVICES AND METHODS OF MAKING SAME

(76) Inventors: Edward P. Lindholm, 52 Londen St., Brookline, MA (US) 02445; Louis Cincotta, 225 River Rd., Andover, MA (US) 01810; Richard A. Minns, 64 Claremont Ave., Arlington, MA (US) 02476-5802; Larry Takiff, 39 Amsden St., Arlington, MA (US) 02474

( * ) Notice: Subject to any disclaimer, the term of this patent is extended or adjusted under 35 U.S.C. 154(b) by 37 days.

This patent is subject to a terminal disclaimer.

(21) Appl. No.: 10/651,627

(22) Filed: Aug. 29, 2003

(65) Prior Publication Data

US 2004/0137188 A1 Jul. 15, 2004

Related U.S. Application Data

(60) Provisional application No. 60/415,480, filed on Oct. 2, 2002, and provisional application No. 60/295,903, filed on Jun. 5, 2001.

(51) Int. Cl.
*B32B 3/02* (2006.01)

(52) U.S. Cl. .................... 428/64.1; 428/64.4; 428/64.8; 430/270.14

(58) Field of Classification Search .............. 428/64.1, 428/64.4, 64.8, 913; 430/270.14, 495.1, 945
See application file for complete search history.

(56) References Cited

U.S. PATENT DOCUMENTS

| | | | | | |
|---|---|---|---|---|---|
| 5,815,484 | A | * | 9/1998 | Smith et al. | 369/275.1 |
| 6,011,772 | A | * | 1/2000 | Rollhaus et al. | 369/286 |
| 6,338,933 | B1 | * | 1/2002 | Lawandy et al. | 430/270.1 |
| 6,343,063 | B1 | * | 1/2002 | Rollhaus et al. | 369/286 |
| 2001/0046204 | A1 | * | 11/2001 | Rollhaus et al. | 369/284 |
| 2002/0102499 | A1 | * | 8/2002 | Krieg-Kowald | 430/321 |
| 2003/0002431 | A1 | * | 1/2003 | Breitung et al. | 369/288 |
| 2003/0129408 | A1 | * | 7/2003 | Thompson et al. | 428/411.1 |

* cited by examiner

*Primary Examiner*—Elizabeth Mulvahey

(57) ABSTRACT

Methods and apparatus are provided for making an optically readable storage media in which the reading beam passes through a bonding layer configured with a reactive material that transforms from an optically transparent state to an optically opaque state after exposure to a predefined stimulus, thereby inhibiting access to the data encoded on the optically readable storage media. The method includes steps of synthesizing a blocked dye combining the blocked dye with a carrier material curing the resultant combination deblocking the dye to produce a reduced dye in the resultant bonding layer exposing the optically readable storage media with the reactive material in its bonding layer to a predetermined stimulus. In a further aspect of the present invention methods and apparatus are provided for making an optically readable storage media wherein the reading light passes through the bonding layer and the data encoded information is encoded on the L1 substrate. In yet another aspect of the present invention methods and apparatus are provided for making an optically readable storage media with at least two mechanisms for limiting access to the encoded data of the optically readable storage media.

29 Claims, 19 Drawing Sheets

| FIG. 21A-1 |
| FIG. 21A-2 |
| FIG. 21A-3 |

Order     : FLEXPLAY.1
Stamper   : C01E1709
Testmode  : normal
Disc time : 3704.484 Layer:A/0[DVD]
EAN cide  :
Q-Class   : Default[CHECK]
Title     : BAOs TEST
Remarks   : BAOs TEST Sysid     : 15-00004061 Ch: 1
Start     : 21.05.2001 74:37 / CS4
Proc.Desc.:
Machine   :
Carrier   : FLEXPLAY
Decision  :

FIG. 21A-2

| CHK |
|---|
| ASYd |
| RES |
| I14V |
| IVD |

| RAD | Min | Max | Avg | 24.0 | 28.2 | 32.5 | 36.7 | 41.0 | 45.2 | 49.4 | 53.7 |
|---|---|---|---|---|---|---|---|---|---|---|---|
| JC | | | 7.4 | 7.3 | 7.2 | 7.3 | 7.5 | 7.5 | 7.5 | 7.5 | 7.7 |
| ASYd | +.0 | 8.0 | -.4 | +1.2 | +.6 | +.2 | -0.8 | -0.8 | -1.0 | -1.4 | -2.2 |
| RES | .24 | +8.0 | .26 | .26 | .26 | .26 | .26 | .26 | .26 | .27 | .27 |
| I14N | | | .91 | .92 | .92 | .92 | .92 | .92 | .92 | .91 | .90 |
| I14V | .64 | .14 | .01 | .01 | .01 | .01 | .00 | .01 | .01 | .01 | .01 |
| R14H | | | .684 | .664 | .672 | .676 | .684 | .696 | .704 | .712 | .712 |
| DPT | .50 | 1.10 | .94 | .91 | .93 | .94 | .95 | .95 | .95 | .94 | .93 |
| DPA | -20.0 | +20.0 | +4.0 | +4.0 | +5.0 | +2.6 | +6.2 | +.8 | +3.4 | +8.2 | +1.8 |
| TCS | .10 | | .23 | .21 | .22 | .23 | .24 | .24 | .24 | .24 | .23 |
| TLC | | | | | | | | | | | |
| I3N | | | .24 | .24 | .24 | .24 | .24 | .24 | .24 | .25 | .24 |
| TPP | | .90 | .21 | .21 | .21 | .21 | .20 | .20 | .20 | .21 | .22 |
| I1Ud | | | .54 | .54 | .54 | .54 | .55 | .56 | .56 | .56 | .56 |
| I14D | | | | | | | | | | | |

| STA | APIE | IVD | BPL0 | BPL1 | BL00 | BL01 | EL00 | EL01 |
|---|---|---|---|---|---|---|---|---|
| Act | 40 | .29 | | 23.95 | | 53.45 | | |
| Min | 60 | .32 | | | | | | |
| Max | | | | | | | | |

| CNT | PIE | PIF | POF | RNSd | TPP | I3N | I14N | R14H | ASYd | RES | JIT |
|---|---|---|---|---|---|---|---|---|---|---|---|
| Min Pos Lmt | 16 49.4 | 0 23.9 | 0 23.9 0 | 3 24.9 | .19 36.1 | .22 36.1 | .25 24.4 | .90 51.1 64 | .660 24.3 | -2.2 53.4 +.0 | +1.4 24.0 +8.0 | -2.4 35.6 +2.4 | 7.2 24.7 |
| Max Pos Lmt | 74 31.9 100 | 14 24.2 36 | 0 OT | 6 36.8 7 | .23 24.2 .90 | .25 24.4 | .93 24.4 | .716 49.2 | +1.4 24.0 +8.0 | .28 49.2 | 7.8 37.8 8.0 |
| Avg Dev | 40 6 | 0 0 | 4 0 | | .21 .01 | .24 .00 | .91 .00 | .684 .008 | -0.4 +.4 | .26 .00 | 7.5 .1 |

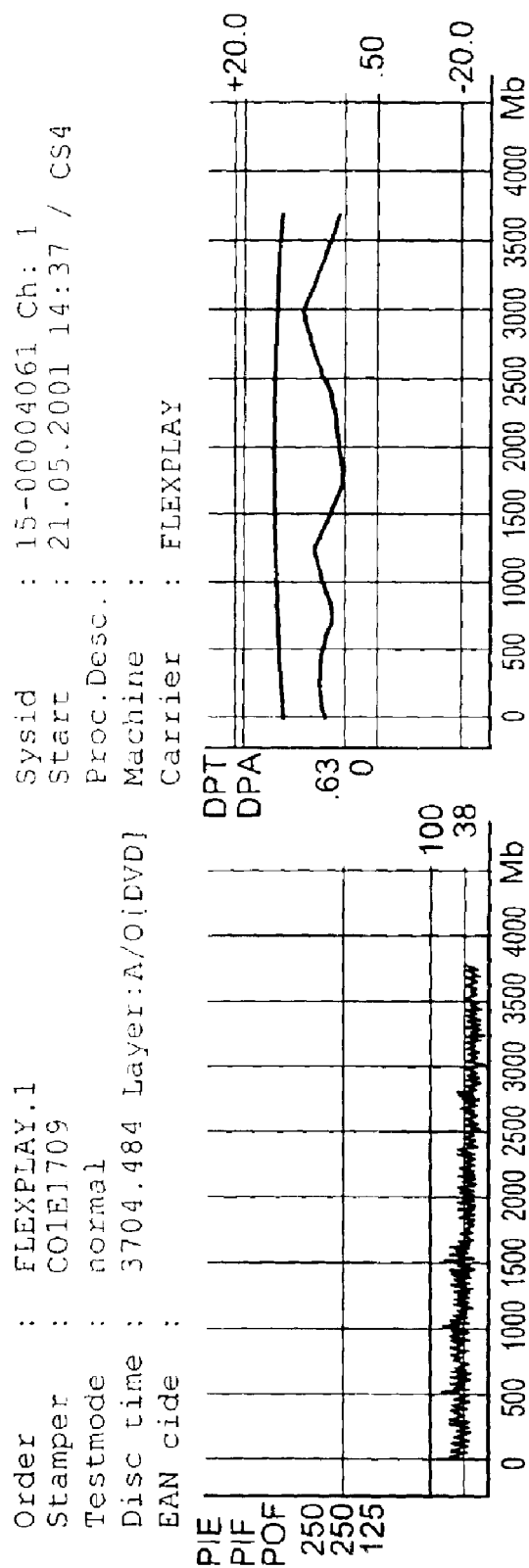
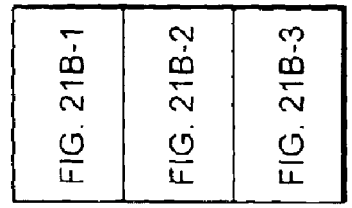
FIG. 21B-1
FIG. 21B

REACTIVE MATERIALS FOR LIMITED PLAY OPTICAL DEVICES AND METHODS OF MAKING SAME

Priority is herewith claimed under 35 U.S.C. §119(e) from co-pending U.S. Provisional Patent Application No. 60/415,480 filed Oct. 2, 2002; and under 35 U.S.C. §120 from copending Non-Provisional Patent Application No. 10/163,474 filed Jun. 5, 2002, which claims priority to U.S. Provisional Patent Application No. 60/295,903 filed on Jun. 5, 2001. The disclosure of all the above Patent Applications is incorporated by reference herein in its entirety.

FIELD OF THE INVENTION

This invention relates to optically readable data storage media and, more particularly, to methods, compositions, and articles of manufacture of optically readable data storage media wherein the data is accessible for a finite period of time.

BACKGROUND OF THE INVENTION

Optical discs such as CDs and DVDs are sold and rented to consumers. The content of the optical discs may be music, movies, video clips, software or data. The purchase price of CDs and DVDs can be high; this reflects the value of the information encoded on the discs, such as movies or software, rather than the manufacturing cost of these optical discs. Frequently, content providers, such as movie studios or software companies, do not want to sell at a low cost copies of their information that will have a long lifetime in the marketplace. Consumers frequently want to access content information only for a brief period and at a low cost: Rentals of CDs and DVDs enable consumers to access content information at a lower cost than if consumers had to purchase the media, but the need to return the physical media is inconvenient. It would be desirable to have limited play/expiring optical media that the user could purchase at a low cost, would address the concerns of the content providers about lifetime of their content in the marketplace, and which would not have the disadvantage of having to be returned, as is the case with videotape movie rentals today. It would also be desirable to manufacture such optical media at low cost and with minimum changes to existing manufacturing processes for optical discs. Finally, in order for the content providers to be willing to provide their content through limited play/expiring optical media, the mechanism that limits playing of the media should not be easily defeatable, enabling access to the content beyond the intended period of use.

Heretofore, the requirements of low cost, limited content lifetime, avoidance of rental returns, resistance to attempts to defeat, and minimum changes to existing manufacturing processes referred to above have not been fully met. What is needed is a solution that simultaneously addresses all of these requirements. One embodiment of the present invention is directed to meeting these requirements, among others.

Several approaches have been proposed to make a limited play (expiring) optical disc based on a layer that changes from a non-interfering ("transparent") state where it does not interfere with the reliable reading of the information on the optical disc to an interfering ("opaque") state where the layer interferes with the reading of the data on the optical disc (e.g., see U.S. Pat. No. 5,815,484 ("Smith et al."), herein incorporated by reference in its entirety, and U.S. Pat. No. 6,011,772 ("Rollhaus et al."), herein incorporated by reference in its entirety. The interference may be due to the layer becoming dark, reflective, highly birefringent, pitting, bubbling, shattering, corroding, bending, changing refractive properties or combinations of these, among other possibilities.

Optical discs with such a layer changing from a transparent to an opaque state in response to a stimulus such as exposure to oxygen in the atmosphere, or the light of the reading laser, can be used to manufacture limited-play optical discs (such as DVDs) that become unusable in a predetermined way (such as within a certain period of exposure to environmental oxygen). Such discs can find a variety of commercial applications, such as the viewing of a video by consumers at a moment chosen by the consumer and without the need to return the expired optical disc.

The interfering layer that renders the disc unplayable by inhibiting the reading of the data can be applied via a variety of techniques to the surface of an optical disc. Such an approach, however, has a number of disadvantages. For example, it may be defeated by finding a way to reverse the transition of the layer to an opaque state, such as exposing the disc to a reducing chemical substance that reverses an oxidation reaction, or by entirely removing the layer through chemical means (such as solvents) or mechanical means (such as polishing or grinding). Also, adding an additional layer can complicate manufacturing of the optical discs, for example by requiring additional capital equipment and additional steps in the manufacturing process, and thus can increase the costs and/or decrease the yields for the manufacturing of optical discs.

A protective layer engineered to resist attempts to defeat the disc can be applied on top of the interfering layer, an approach that has been used by at least some of the present inventors. However, this introduces still another step in the manufacturing process, further adding to costs and possibly further reducing manufacturing yields. Furthermore, since the protective layer would still be at the surface of the disc, it could still be removed by chemical means (such as solvents) or mechanical means (such as polishing or grinding), of could be defeated by chemical substances that could diffuse through the protective layer and reach the reactive layer.

As explained above, when manufacturing expiring optical discs, it is desirable to employ a cost effective manufacturing process and to make discs that are not easily defeatable. In addition, it is desirable for the disc to make a rapid transition from the playable to the expired state. Among other benefits, this would reduce the variation of the playing period among optical media players and drives, despite the fact that there is substantial variability in the ability of the players and drives in the market to play discs with a given deterioration in their physical playability characteristics (such as the reflectivity to the light of the reading laser).

SUMMARY OF THE INVENTION

Under a first aspect of the present invention limited play optical devices are provided with an interstitial reactive layer and methods of making same.

Under a second aspect of the present invention a method is provided for authoring a master to produce a substrate of a multi-substrate, optically-readable storage medium wherein a topology having a plurality of pits and lands is used to create an inverted version of the topology in which said inverted version of the topology is used as the topology of the master.

Under a third aspect of the present invention a method is provided for forming a multi-substrate, optically-readable storage medium, wherein the medium has information defined as a plurality of pits and lands on an upper substrate and said information is to be read by light being transmitted through a lower substrate wherein an adhesive layer bonds the upper substrate and lower substrate together.

Under a fourth aspect of the present invention a data storage device is provided having a first substrate halving defined thereon a plurality of pits and lands covered by a reflective material and a second substrate wherein a bonding layer containing a reactive agent, which inhibits transmission of light in response to a predetermined stimulus, resides between the first substrate and the second substrate.

Under a fifth aspect of the present invention an adhesive is provided for bonding a first substrate and a second substrate, wherein said adhesive comprises a carrier material and a reactive material that renders the data encoded substrate unreadable.

Under a sixth aspect of the present invention a mechanism is provided that causes the data stored on an optically-readable data storage medium to first become unreadable and second destroyed.

Under a seventh aspect of the present invention an optically-readable data storage medium is provided having a first substrate and a second substrate, wherein at least one of said first substrate and said second substrate has information encoding features, and a bonding layer between first substrate and second substrate in which said bonding layer comprises a carrier material and a reactive material where said reactive material changes from a transparent state to an optically opaque state as a result of a predefined stimulus.

Under a eighth aspect of the present invention a method making an adhesive is provided for bonding a first substrate and a second substrate wherein a blocked dye is combined with a carrier material in which said blocked dye is subsequently unblocked resulting in the reduced form of the unblocked dye.

Under another overlapping embodiment of the present invention a class of compounds as shown below is described

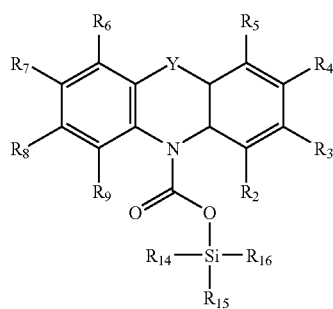

(I)

wherein

Y is O, S, Se, $CR_{17}R_{18}$, $NR_{13}$, wherein $R_{13}$, $R_{17}$, $R_{18}$ is each independently selected from hydrogen, $C_1$–$C_3$ alkyl and substituted aryl groups and unsubstituted aryl groups;

$R_2$, $R_5$, $R_6$, and $R_9$ each is independently selected from hydrogen, halogen, $C_1$–$C_6$ alkyl, $C_1$–$C_6$ alkoxy, aryl, nitro, azo and fused aromatic groups;

$R_3$, $R_4$, $R_7$, and $R_8$ each is independently selected from $NR_{10}$, $R_{11}$, $OR_{12}$, hydrogen, alkyl, aryl, azo, and fused aromatic groups; and $R_{10}$, $R_{11}$, $R_{12}$, $R_{14}$, $R_{15}$ and $R_{16}$ each is independently selected from hydrogen, unsubstituted $C_1$–$C_6$ alkyl, substituted $C_1$–$C_6$ alkyl, unsubstituted $C_1$–$C_6$ alkoxy, and substituted $C_1$–$C_6$ alkoxy, benzyl or aryl groups.

DETAILED DESCRIPTION

Certain optical discs, such as DVDs, consist of two plastic halves ("substrates"), which are metallized and bound together with an interstitial bonding layer. It would be desirable to use an interstitial layer between the two substrates to interfere with the reading laser in order to inhibit reading of the disc. This would result in a disc that is more difficult to defeat, as the two halves of the optical disc would protect the interfering layer. Using an interstitial layer as the interfering layer still allows triggering the process of disc expiration. For example, polycarbonate, which is typically used to manufacture DVD substrates, allows the propagation of oxygen that could reach the interstitial reactive layer and trigger a reaction that causes the expiration of the disc.

Figure 2:
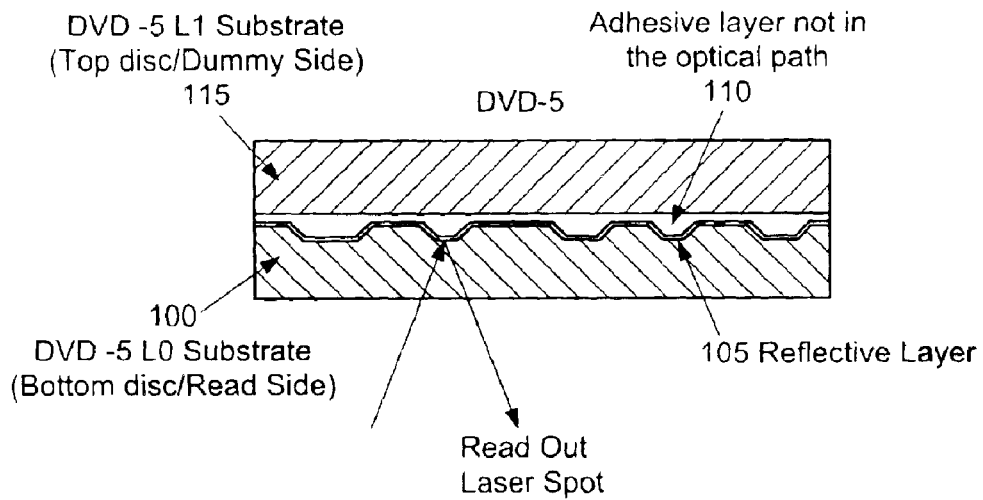
FIG. 2 is a schematic cross sectional view of a single layer DVD-5 disc.

Furthermore, it would be desirable to use the bonding layer itself as the interfering layer, for example by changing the chemical composition of the bonding layer through the incorporation of a reactive substance. This could simplify the manufacturing of limited-play optical discs because no additional layers would be introduced, and attempting to defeat the limited-play mechanism by removing this layer could destroy the optical disc itself, as the bonding layer is critical to the integrity of the optical disc. However, in certain types of optical discs, such as a DVD-5, the bonding layer is not in the optical path. FIG. 2 illustrates a cross sectional view of the layers typical of a DVD-5 construct. Thus while the bonding layer could play part in an expiration process for a DVD-5 that does not rely on direct interference with the reading laser (e.g. by corroding the reflective metal layer that is in contact with the bonding layer), it would not be possible to make this type of disc expire by transitioning the bonding layer to a state that prevents the reading laser from reading the data on the disc. Since it is often desirable to make the disc unplayable by means of a process that interferes with the reading laser, it is desirable to have a disc similar to a DVD-5 where the interstitial bonding layer is in the optical path.

In limited use optical discs where the expiration process relies on interference with the reading laser, the data encoding structures (such as metallized pits on a polycarbonate substrate) typically are preserved in an expired disc, although the reading laser is prevented from reading the encoded information. As long as these data structures are present, there is always the possibility of the disc being defeated by enabling the reading laser to access the information. It would thus be desirable to have additional mechanisms that prevent recovery of the data, such as permanently erasing the data by compromising the integrity of the data structures on the optical disc.

These, and other, goals and embodiments of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

A clear conception of the advantages and features constituting the present invention, and of the components and operation of model systems provided with the invention, will become more readily apparent by referring to the exemplary, and therefore non-limiting, embodiments illustrated in the drawings accompanying and forming a part of this specification. It should be noted that the features illustrated in the drawings are not necessarily drawn to scale.

We now describe the different aspects of the current invention, and several corresponding embodiments and examples.

Figure 1:
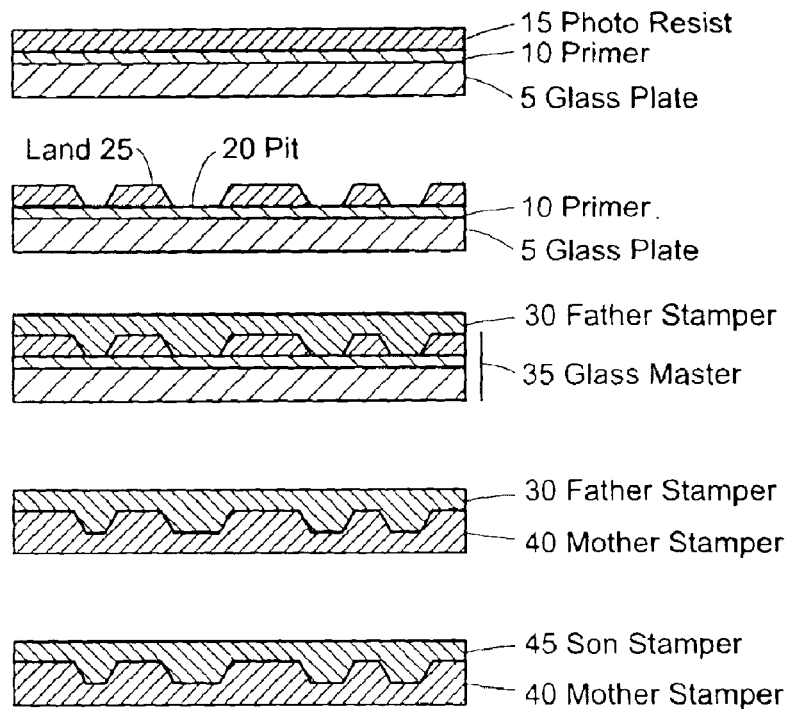
FIG. 1 is a schematic cross sectional view of select stages in the process of creating a physical stamper used in replicating DVD-5 substrates.

DVDs are the most common optical discs used for distribution of movies. DVDs are made from two bonded plastic substrates, typically referred to as L0 for the bottom substrate and L1 for the top substrate, where "top" and "bottom" refer to a DVD in a playing position where it is read from the bottom, as is the common convention. These substrates are molded from materials such as polycarbonate, acrylic, or polyolefine, which is injected in a molten form to a mold and pressed against a stamper. The process of creating the physical stampers used in replicating the DVD substrates is referred to as Mastering. The following procedure is used, which is illustrated in FIG. 1:

1. Float glass blank 5 is polished and coated with a primer 10 to enhance adhesion with the photo resist layer 15.
2. Photo resist coating 15 is applied, baked, and then exposed to the laser for recording. The formatted data signal is used to modulate the cutting laser of a laser beam recorder (LBR) machine which creates pits 20 in the glass disc.
3. The exposed glass is then developed leaving pits 20 and lands 25 across the surface.
4. This "Glass Master" then has a thin (110 nm) metal layer sputter-applied to make the surface conductive for electroplating.
5. The glass master is then placed into an electroplating solution where nickel is formed to the desired thickness. (Typically 0.300 mm).
6. This "Metal Father" (or "father stamper 30") is then separated from the glass master 35 and cleaned. At this step, the metal father 30 could be used for the molding process, but if the part gets destroyed or damaged in replication, the entire process must be repeated.
7. Therefore, most manufacturers will grow "Metal Mothers" (or "mother stampers 40"), which are negatives of the father 30. Typically, four mother stampers 40 can be grown from one father 30 without quality degradation, and from each mother 40, up to 8 stampers ("sons 45") can be grown.
8. Stampers get sent to replication facilities and mothers 40 are stored for reorders or replacement parts.

Figure 3:
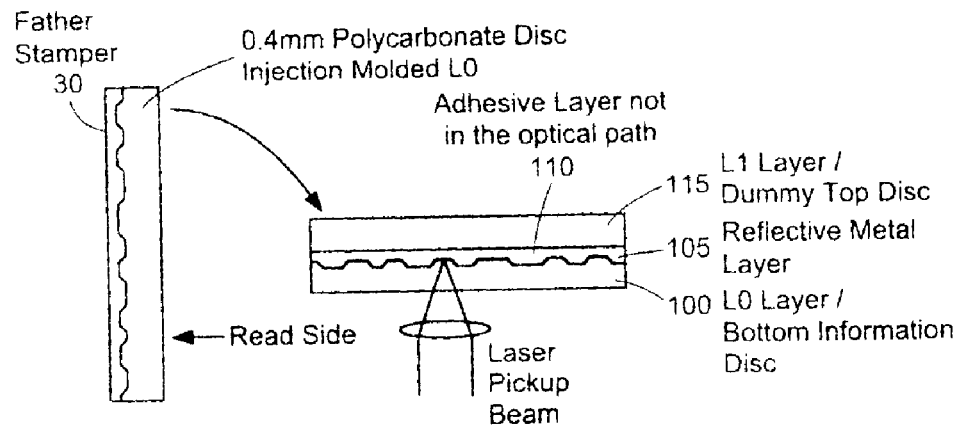
FIG. 3 is a schematic cross sectional view illustrating the manufacturing and reading of a standard DVD-5.

In the case of a DVD-5, which is a single layer disc illustrated in FIG. 2, the L0 substrate 100 is covered with a thin reflective layer 105 of aluminum by a sputtering process. This creates a metallic coating between 60 and 100 angstroms thick (the L0 layer). The L0 substrate 100 is then bonded 110 to a blank L1 substrate 10, as illustrated in FIG. 3. For a DVD-9, which is a two-layer disc, the L0 layer is formed as a very thin, semi-reflective metal layer, and is typically made of gold. A fully reflective aluminum layer is formed on the L1 substrate (the L1 layer). The two substrates are subsequently bonded with appropriate adhesive material, which forms a transparent bonding layer, to form the DVD-9 disc.

Figure 4:
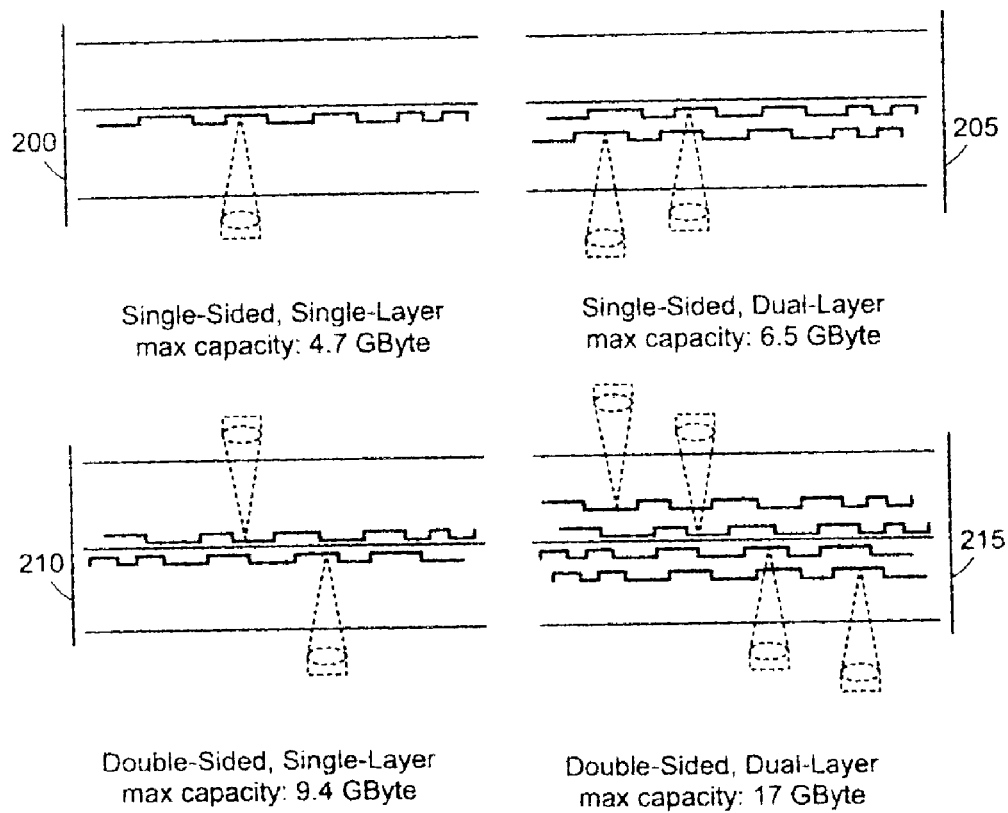
FIG. 4 is a diagram representing single sided single layer, single sided double layer, double layer single sided, and double layer double sided DVD constructs.

As seen in the DVD family illustration in FIG. 4, a DVD disc may contain either one or two information layers for each substrate, resulting to different types of disc capacities, such as DVD-5 200 (single sided, single layer, 4.7 Gbyte capacity), DVD-9 205 (single sided, dual layer, 8.5 Gbyte capacity), DVD-10 210 (double sided, single layer, 9.4 Gbyte capacity), DVD-14 (double sided, one side single layer, one side dual layer, 13.2 Gbyte capacity), and DVD-18 215 (double sided, dual layer, 17 Gbyte capacity).

Standards bodies have been established that suggest, recommend and/or dictate specifications for the various disc formats and/or disc data capacities to insure that the different disc formats and/or disc data capacities play and/or are read by the various media players distributed by media player manufacturers. Examples of standards bodies include, but not limited to, the DVD Forum (www.dvdforum.org) and European Computer Manufacturers Association ("ECMA") (www.ecma-international.org).

Figure 5A:
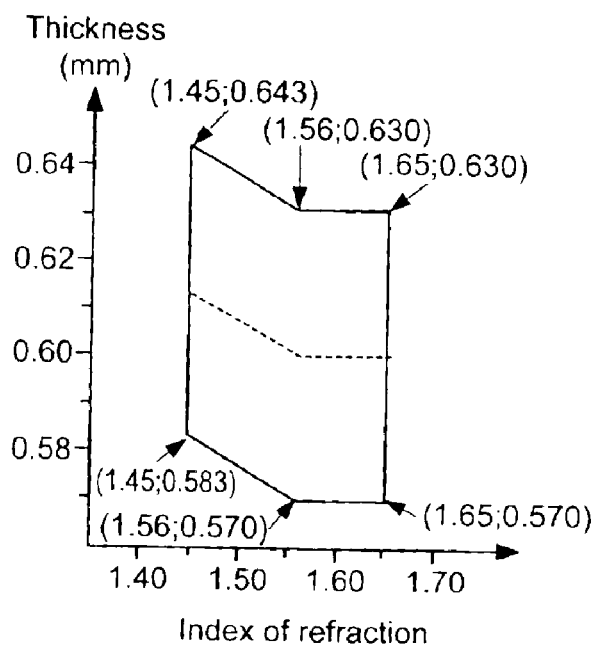
FIG. 5 is a graphic depicting the index of refraction as a function of substrate thickness for single layer and double layer DVDs.
Figure 5B:
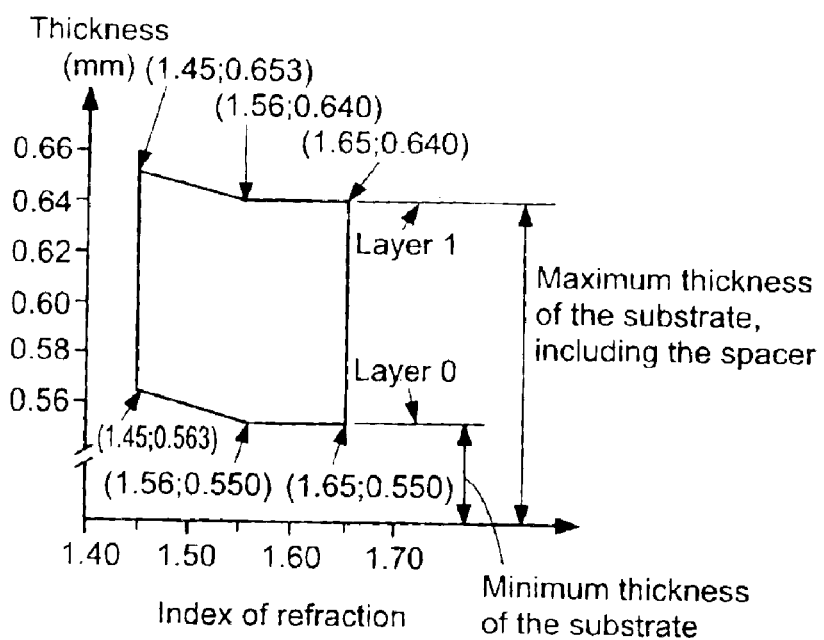

For example, a dual layer disc such as a DVD-9 205 must conform to the "DVD Specifications for Read-Only Disc, Part 1 Physical Specifications Version 1.0", which require the following:

1. Total Disc thickness, including bonding layer 110, spacer(s) and label(s), shall be 1.20 mm+0.30 mm/−0.06 nm
2. Index of refraction (RI) of the transparent substrate shall be 1.55+/−0.10 The index of refraction of the spacer shall be (RI of the substrate+/−0.10)
3. Thickness of the transparent substrate is specified as a function of its index of refraction. Typically with polycarbonate at RI=1.56, the thickness values for the disc substrate would be 0.57 mm~0.63 mm (see FIGS. 5A and 5B)

The standards bodies do not directly provide a specification for the spacer layer (bonding layer 110) thickness for DVD-5 200 and DVD-10 210 formats as long as the total disc thickness conforms to the DVD specification and the half discs (molded substrates) conform to RI related specifications as above.

The information in DVDs is encoded in the pits 20 and lands 25 (data areas that are not pits) that are molded into the substrates and subsequently are metallized to form the corresponding data layer. The pits and the lands are organized in a spiral track, which, in the case of a DVD-5 200, is read in a clockwise direction beginning at the inside of the disc and proceeding towards the outside of the disc. The reference area of the disc that is not occupied by data is used for tracking of the reading laser. The reading laser, which has a wavelength of 630–650 nanometer in vacuum, is focused on the L0 layer 100 of a DVD-5 200 or DVD-9 205, or on the L1 layer 115 of a DVD-9 by penetrating through the semi-reflective L0 layer 100, and it is reflected back to a photo detector. During transitions from a pit 20 to a land 25 or vice versa, interference patterns develop, which are detected by the photo detector and result in changes in its electrical output. These changes in the electrical output of the photo detector allow the player to read the information recorded on the DVD.

Figure 6:
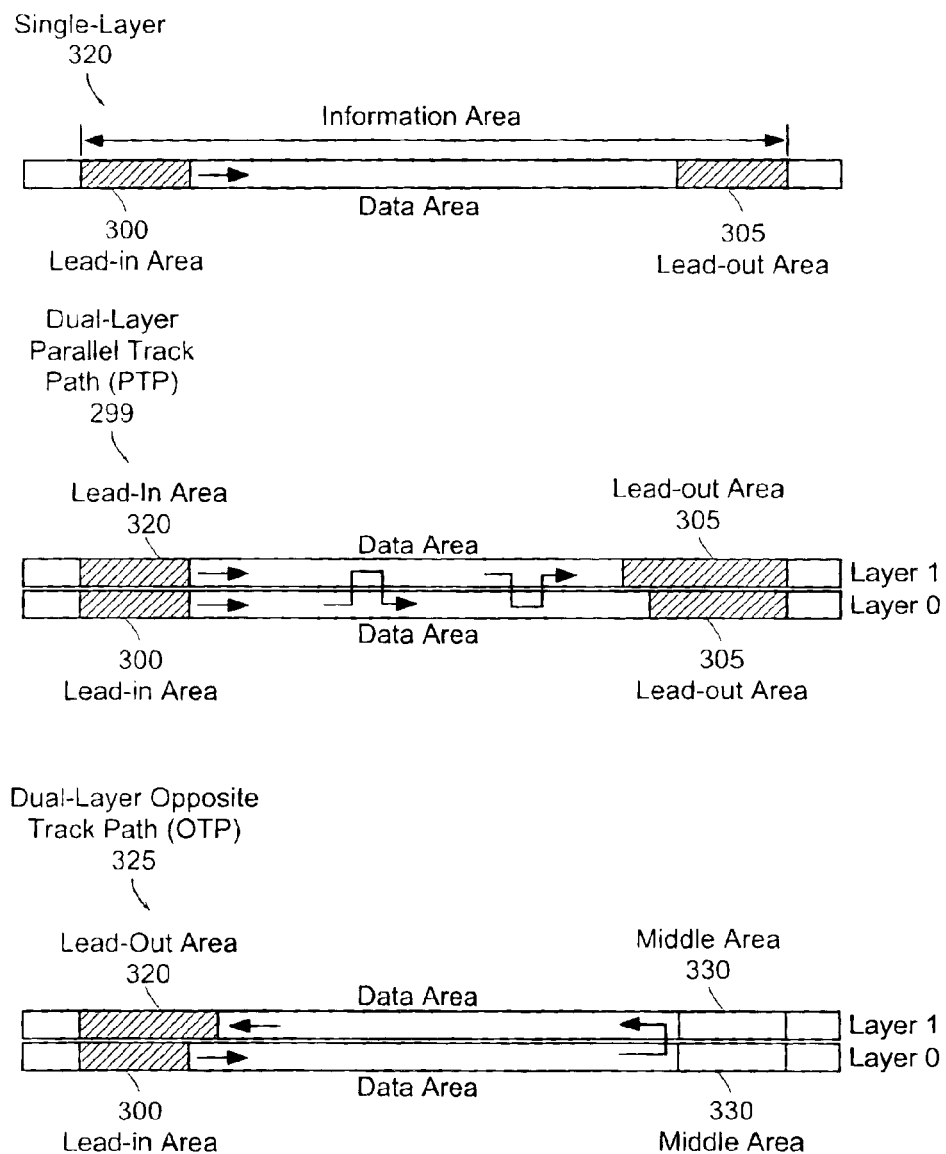
FIG. 6 is a schematic illustrating the read-out possibilities for single-layer and dual-layer DVDs.

Dual-layer discs, such as DVD-9s 205, typically utilize one of two methods for read-out of the disc information:

A dual-layer Parallel Track Path (PTP) disc 299 will have a Lead-in 300 and a Lead-out 305 area on both layers, as illustrated in FIG. 6. For each layer, the lead-in 300 area is located at the inner radius of the disc, and lead-out 305 area is located at the outer radius of the disc. This layout structure is comparable with the layout of the single layer 320 disc. Reading of the data is done, as in a DVD-5, 200 from the inner radius of the disc to the outer radius, for both layers. With propel authoring of the content on the disc, the PTP method can allow quick access from layer to layer, for example in order to provide background information and commentary in one track along with the movie in the other track.

A dual-layer Opposite Track Path (OTP) 325 disc, also illustrated in FIG. 6, offers the possibility of seamless continuation of the playback from the L0 100 to the L1 115 layer. The first information layer (L0) 100 starts with a lead-in area at the inner radius of the disc and ends with a so-called middle area 330 at the outer radius. The second information layer starts with a Middle Area 330 at the outer radius and ends with a lead-out 300 area at the inner radius of the disc. Reading the data 335 stored on the disc will start at the inner radius of the first information layer and proceed until the Middle Area 330 of this layer is reached. Then a switch over to the Middle Area in the second information layer is made, in order to continue reading of the data from the outer radius up to the lead-out 305 Area in the inner radius of the second layer (L1) 115.

Single Layer Optical Discs

Figure 7:
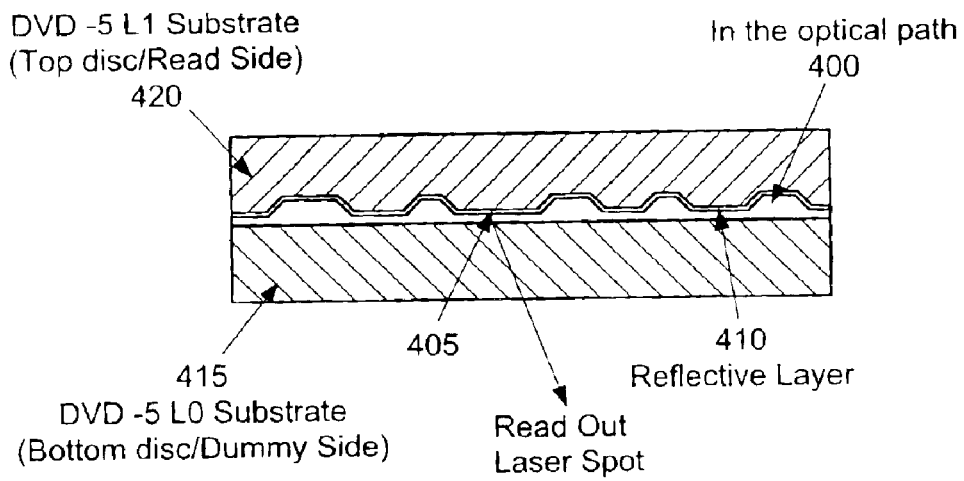
FIG. 7 is a schematic cross sectional view illustrating a modified DVD-5 construct with the bonding layer in the optical path of the reading laser.

One embodiment of the present invention is an optical disc similar to a DVD-5 where, unlike a standard DVD-5, the interstitial layer 400 typically used as the bonding layer 401 is in the optical path 405 of the reading laser (e.g., see FIG. 7). In one embodiment of the present invention (labeled below as "Special DVD-5 design #1"), this disc is manufactured by inverting the reflective layer 410 of a standard DVD-5, and reading the information through the non-information-bearing substrate 415 and the bonding layer 401. In another embodiment of the present invention (labeled below as "Special DVD-5 design #2"), the direction of the spiral track is inverted during mastering, the information bearing substrate is flipped "upside down", and the information is read through the non-information bearing substrate 415 and the bonding layer 401. In this type of optical disc, the bonding layer 401 is an integral part of the optical path 405 of the reading laser. Even though the structure of the "Special DVD-5" disc described herein differs from a standard DVD-5, a player would play this disc as if it were a standard DVD-5.

This embodiment of the present invention has significant advantages in terms of allowing the manufacturing of a low-cost "limited-play" optical disc that is resistant to attempts to defeat it. In particular, because it does not incorporate any additional layers compared to a standard DVD-5, it can be manufactured on equipment designed to manufacture DVD-5 discs with minimal changes to that equipment. Furthermore, because the bonding layer 401 is in the optical path, 405 modifying that layer to interfere with the reading of data in response to a predetermined stimulus results in a disc that is very difficult to defeat, as the interfering layer 400 is protected by the two substrates 415 and 420, respectively of the optical disc. For example, grinding the interfering layer 400 off the disc is impractical, as it would most likely destroy the disc. Similarly, attempting to compromise the bonding/interfering layer in other ways is likely to destroy the structural integrity of the optical disc.

We now describe in detail the manufacturing of three embodiments of the current invention, which we label as "Special DVD-5" designs 1, 2 and 3.

Special DVD-5 Design #1

Figure 8:
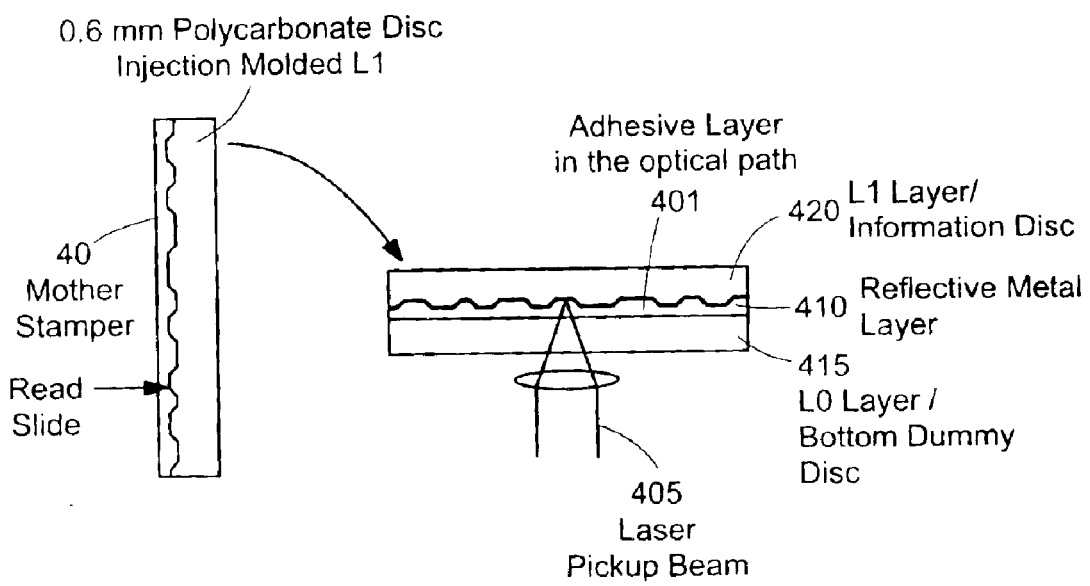
FIG. 8 is schematic cross sectional view illustrating the manufacturing and reading of an altered DVD-5 construct with the bonding layer in the optical path of the reading laser in which the mother stamper was used to mold the L1 substrate.

In one embodiment of the invention, the above process is modified by using the mother stamper to replicate the L1 disc substrate 420. FIG. 3 shows how the stamper or father is used to mold a normal single layer DVD-5 substrate. FIG. 8 illustrates manufacturing this embodiment of the current invention by using the mother stamper 40 and creating a disc with the bonding layer 401 in the optical path 405.

Figure 9:
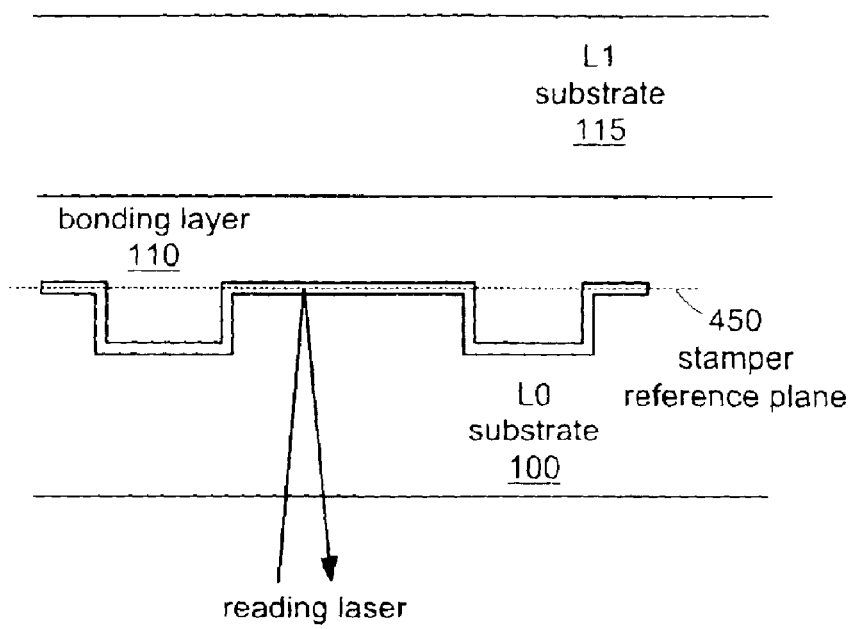
FIG. 9 is a schematic cross sectional view illustrating the stamper reference plane of a standard DVD-5 construct wherein the pits and lands are molded in the L0 substrate.
Figure 10:
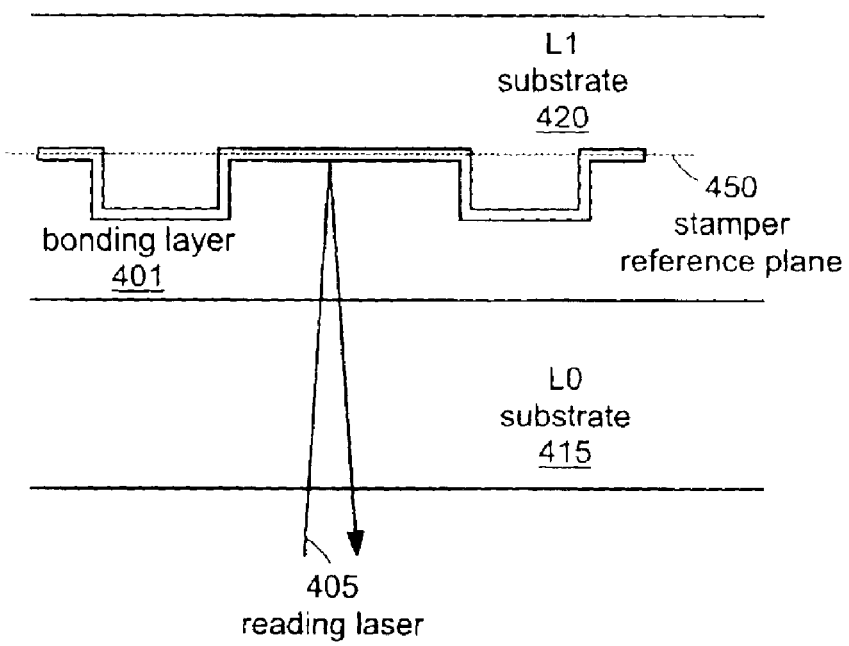
FIG. 10 is a schematic cross sectional view illustrating the stamper reference plane of a modified DVD-5 constrict wherein the pits and lands are molded in the L1 substrate.

In a normally molded standard DVD-5 information is encoded on the L0 100 side with "pits" 20 and "lands" 25 molded on the L0 substrate 100 and metallized with a reflective metal coating, 105 as illustrated in FIG. 2, FIG. 3 and FIG. 9. In one embodiment of the current invention, the mother stamper 40 is used to mold the L1 side 420 as shown in FIG. 8. This side is subsequently metallized and bonded with a blank L0 substrate, 415 leaving the bonding layer 401 in the optical path, 405 as shown in FIG. 10. Using the specified layer thickness of 0.055 mm+/−0.015, the thickness of the L0 substrate 100 is targeted at 0.55 mm~0.57 during molding, to yield a focal length of the disc thickness (including the bonding layer) consistent with standard DVD specifications, allowing the player to be in the normal focusing range for reading at L0 layer 100. Thus the player interprets the disc as a standard single layer DVD-5. Field experience has shown that spacer layer thickness can be maintained at 0.045~0.065 mm consistently in production. This controlled variation in production along with the reduced thickness of the molded disc keeps the focus and optics within the specifications set by the DVD licensing authority and the hardware manufacturers (i.e., DVD Forum).

For the replication facility, most applications would remain unchanged in the actual pressing and bonding portions of production. The main areas of change would be in the LBR (laser beam recording) and developing areas of mastering. Typically, masters are cut with larger pit volumes to compensate for plastic shrinkage and replication inefficiencies. The ratio of pit to land areas on a disc is measured by a term called asymmetry. Because asymmetry is a ratio of pit to land area, and because for each pit area, typically defined by I3 to I14 pit, there is an equal and opposite land area I3 to I14 land, typically it is easier for manufacturers to target a positive asymmetry (larger pit area) to account for loses in replication to the plastic substrate. For example, the master may be cut with a positive 10~12% for asymmetry, while the end result from molding may be 5~7%. The specification for the disc substrate is: $-0.05 \leq$ asymmetry $\leq +0.15$. In the case of DVD discs, a positive asymmetry represents a larger pit volume compared with the land area.

For this embodiment of the invention, it may be desirable to change the asymmetry set point on the LBR to produce a higher asymmetry value on the father stamper while subsequently increasing the asymmetry on the mother stamper used for molding. Asymmetry can be changed on the master by modifying the power of exposure, focusing intensity and offset, developing time/endpoint detection, or baseline (control of how fast the laser diode cuts the laser exposure beam off between exposure). There are many other possible ways to control asymmetry, but the basic process or set point control would be the easiest to implement. This process of molding from the mother stamper would also eliminate the need to grow additional stampers and the subsequent yield loses attributed to the family process.

Figure 11:
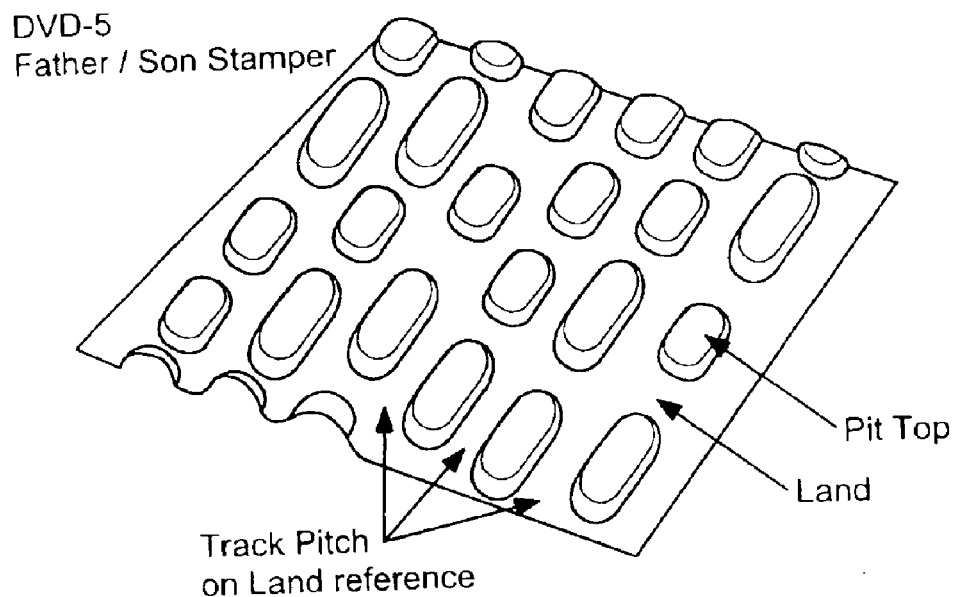
FIG. 11 is a graphic depicting an atomic force microscope image of a DVD-5 father stamper.
Figure 12:
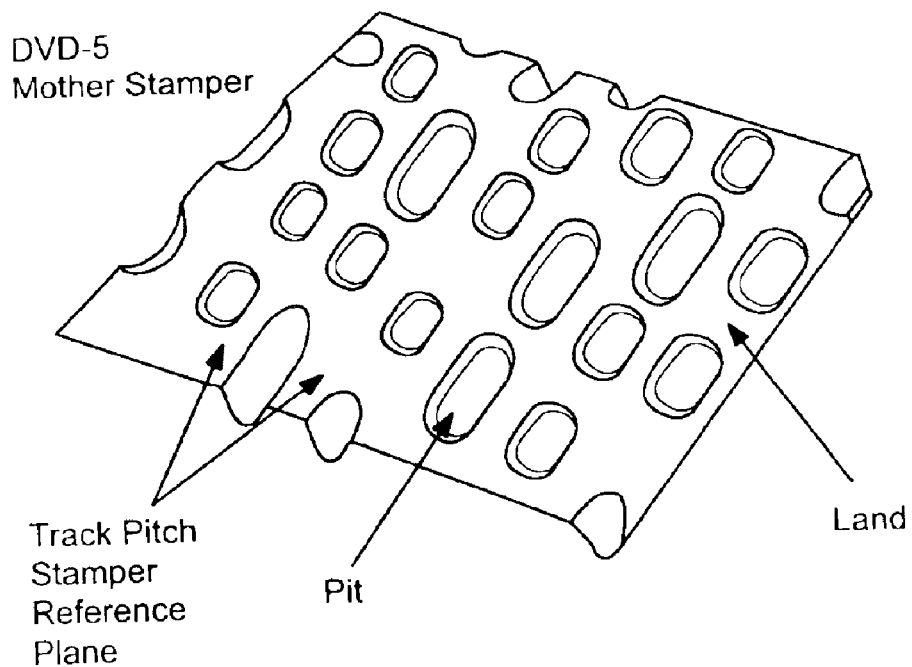
FIG. 12 is a graphic depicting an atomic force microscope image of a DVD-5 mother stamper.
Figure 13:
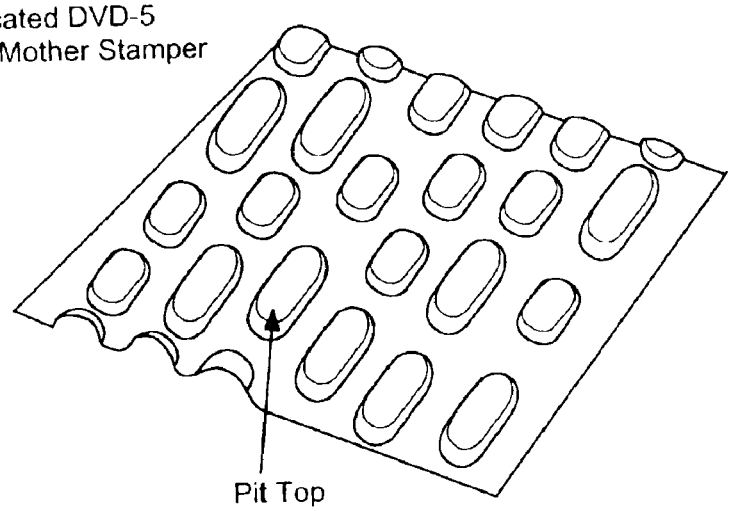
FIG. 13 is a graphic depicting an atomic force microscope image of the L1 layer of a modified DVD-5 that was molded from a mother stamper.

In this embodiment of the invention, the pits 20 are molded in the L1 layer 420 using a mother stamper, 40 and as a result the surface of the pits 20 is elevated relative to the reference plane 450 of the L1 layer 420 as illustrated in FIG. 10. This reference plane 450 is typically used for tracking by the disc player (tracking area). By contrast, in a normal DVD-5 the pits 20 are molded as cavities in the L0 substrate 100 as illustrated in FIG. 9. Using the common convention of describing a disc as if it is in a play position where it is read from the bottom, and a convention that we will follow hereinafter unless otherwise specified, in a normal DVD-5 the pits 20 are lower than the reference plane 450, while the lands 25 are at the reference plane 450 (see FIG. 9). In the embodiment of the invention described above the blank L0 substrate 415 and the bonding layer 401 are below the L1 substrate 420 in the optical path 405 of the reading laser, and the surface of the pits 20 in the L1 substrate 420 is below the reference plane 450 while the lands 25 are at the reference plane 450 (see FIG. 10). Note that this construction requires the pits 25 to be molded in an unconventional way (they protrude from the reference plane 450 of the disc), which is achieved by molding the L1 substrate 420 from a mother stamper 40. FIG. 11 shows an Atomic Force Microscope (AFM) image of a Father stamper 30 for a DVD-5, FIG. 12 shows an AFM image of the corresponding Mother stamper 40, and FIG. 13 shows an AFM image of the L1 layer of a Special DVD-5 Design #1, molded from the Mother stamper 40.

This molding required for this embodiment of the invention can present certain challenges. In a typical injection molding process, the polymer material flows around the pits 20 on the stamper, which are raised from the reference plane 450. This is easier than to mold from the mother, where the polymer material must flow into cavities that will form the pits 20 on the separated part. As the material flows over the surface of the mother stamper 40, the molecular chains cool off through contact with the relatively colder reference surface of the stamper. After the mold is completely filled, then pressure must be applied to bend and force the cooler polymer material into the pit 20 cavities. Although this method is capable to reproduce discs within the specifications of a standard DVD-5 configuration, the molding process is more difficult. However, one skilled in the art can address such challenges by adjusting the process characteristics of the molding machine, e.g., by increasing mold surface temperature and cycle time. Alternatively appropriate materials with higher melt flow rate could be used, such as PMMA or high melt flow rate polycarbonate. For example, General Electric's SPOQ research grade polycarbonate has twice the melt flow rate of standard grade polycarbonate.

As long as the index of refraction (RI) of the bonding adhesive used is approximately equal to the RI of the L0 substrate 415, the thickness of the bonding layer 401 is uniform, and the thickness of the L0 substrate 415 has been adjusted to compensate for the presence of the bonding layer 401 in the optical path 405 of the reading layer, the player will not be able to distinguish Special DVD-5 Design #1 from a standard DVD-5. Experience has shown that playable discs can be manufactured even without these adjustments, because most players will play discs that do not fully conform to the DVD specification (e.g., DVD Forum and/or ECMA), as long as the departure from the specification is not excessive.

EXAMPLE 1

Special DVD-5 Design #1

A father stamper 30 was mastered with slightly increased symmetry (positive asymmetry=larger pits 20 compared to lands 25). The asymmetry can be increased or decreased many ways. The simplest method and the one used for this design, was to increase the development time (endpoint detection set point) to overdevelop the pits 20. By lengthening the development process, the pit volume surrounding, that which was exposed, will increase in volume causing a shift to positive asymmetry.

A mother Stamper 40 was grown from the father stamper 30 as with a normal family process. Disc substrates were molded from the mother stamper 40, taking advantage of the larger indentation caused by the positive asymmetry. The larger pits 20 that resulted from molding with the mother 40 helped to compensate for the additional shrinkage of the pit 20, which is now an extremity to the body of the substrate, rather than a cavity as in the standard molding process. Typically, the molten plastic flows around the pits 20 in a normal (father 30 or son 45) stamper like a river flows around a hill. As the level rises, the hill or the pit 20 will be covered. As the molten plastic flows across the cooler stamper surface, a skin layer forms right on the surface that acts as a heat insulator. This allows for the plastic to maintain its flow rate necessary to form the pit volume without undue stress or cooling. In the case of Special DVD-5 design #1, the plastic has to flow into the indentations of the mother stamper 40, rather than around the bumps of a father/son stamper 30 and 45 respectively. This is difficult because as the plastic flows across the surface of the mother stamper 40, it again forms a skin layer on the surface. Then as the mold volume increases with continued injection and packing/holding time, the molten plastic must be forced into the indentation. Because this skin layer is solidified typically below the glass transitional temperature of the plastic, the material does not free flow into the indentation. Because the pit-forming plastic in the L1 substrate 420 of Special DVD-5 design #1 is not in the optical path of the reading laser, the material can be filled with greater force without the concern for birefringence and residual stress, although there is a limit to the pressure due to warping (tilt) caused by excessive packing pressure on the plastic. In this example, the combination of larger indentations in the mother stamper 40 as well as increased mold temperatures assisted in replicating the desired pits 20. Typically, in direct water injection systems for the mold heating and cooling, safety interlocks of 120° C. max temperature limit the temperature of the water. By using a 50/50 solution of glycol and water, the temperature can be effectively run at max temperature of 130° C. This added temperature assists in keeping the skin layer in the molten state, close to its glass transition temperature, which facilitates the replication of L1 substrates 420 for Special DVD-5 design #1. Also, the mother stamper 40 must be filled quickly with molten plastic in order to prevent skinning on the surface.

L1 substrates 420 were molded as above using a mother stamper 40. FIG. 13 shows an Atomic Force Microscope (AFM) image of an L1 layer 420 molded from a mother stamper 40. FIGS. 11 and 12 show AFM images of the father 30 and mother 40 stampers used in the process. For these discs to be formed, it was necessary to raise the melt temperature from 360° C. to 390° C. while maintaining a mold temperature of 121° C. compared to the standard of around 100° C. The clamp force was set at maximum of 30 tons and the filling time was decreased from 0.13 to 0.09 seconds. These parameters were adjusted until the proper pit 20 formations were achieved.

The molded L1 substrates 420 were bonded using optical grade UV curable DVD adhesives, as used in DVD-9 production, to blank L0 substrates 415, to manufacture design #1 of the Special DVD-5. L0 substrates 415 were molded at a thickness of 0.55~0.57 mm (i.e., 30~50 micron thinner than standard DVD halves) to compensate for the bonding layer in the optical path, thus preserving the same focal depth for the information-carrying layer as in a standard DVD-5.

Special DVD-5 Design #2

The electronics of optical media drives, including DVD players, are typically designed to read the information contained in a layer on the disc by identifying the interference patterns caused by transitions from a "land" 25 to a "pit" 20 in that layer. The pits 20 are often molded with a height approximately equal to, and typically somewhat less than, one quarter of the wavelength of: the reading laser. For example, in DVDs the typical wavelength of the reading laser is 635–650 nanometers (in vacuum), or 410–420 nm in a material with RI=1.55 (which is typical of the materials used to manufacture the DVD substrates), and thus the height of the pits 20 in a standard DVD-5 should be approximately 100–105 nanometers. Consequently, a transition from a land 25 to a pit 20 or vice versa corresponds to a change to the path of the reading laser of approximately one half wavelength, or a phase change of approximately 180 degrees. Two identical waves with a phase difference of 180 degrees will interfere with each other and cancel out, and the electronics of the optical drive are designed to detect the resulting interference patterns. Using the standard convention of the disc being read from below, in a standard DVD-5 the surface of the pits 20 is below the surface of the land 25, and a transition from a land 25 to a pit 20 is a "down" transition, while a transition from a pit 20 to a land 25 is an "up" transition. If the height of the pits 20 is one quarter of the wavelength of the reading laser then a transition from a land 25 to a pit 20 in a standard DVD-5 is a "down" transition that corresponds to a phase change of +180 degrees, and a transition from a pit to a land 25 is an "up" transition that corresponds to a phase change of –180 degrees. If all "up" and a "down" transition differ by 360 degrees, as in the case described above, their effects will be identical. One implication of this is that the pits 20 of a DVD-5 could be molded in the opposite direction, i.e., with the pit surface approximately one quarter wavelength above the land 25 surface, and the electronics of the optical disc player are unlikely to be influenced by whether a detected transition is in the "up" or "down" direction, i.e. whether a pit 20 area is higher or lower than the land 25 area.

Figure 14:
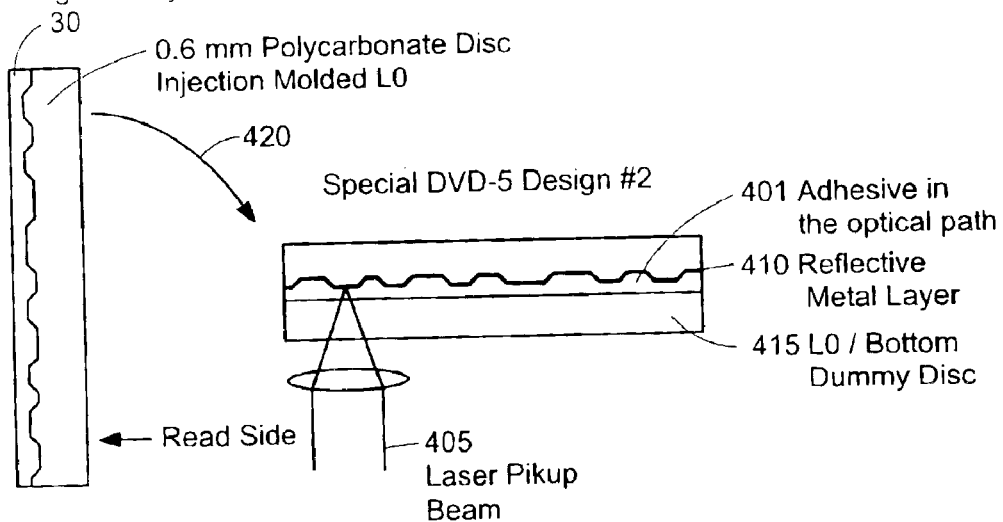
FIG. 14 is a schematic cross sectional view illustrating the manufacturing and reading of a modified DVD-5 in which the L1 layer was molded from a father stamper wherein the direction of the spiral track was reversed during mastering.
Figure 15:
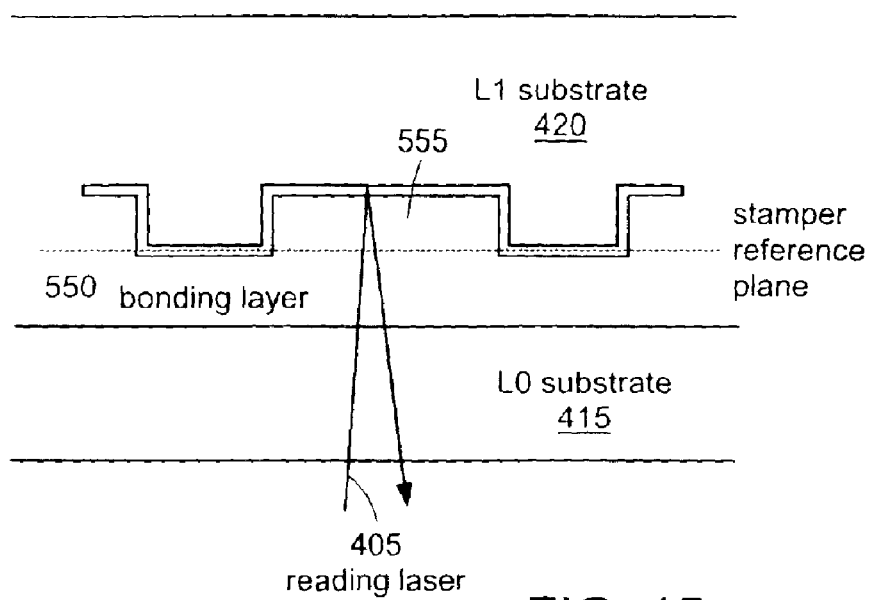
FIG. 15 is a schematic cross sectional view illustrating the stamper reference plane of a modified DVD-5 construct wherein the pits are above the surfaces of the lands and the lands are at the reference plane of the L1 substrate.

In a standard DVD-5, the laser pick up will read through the L0 substrate 100 focusing on the pits 20 aligned in a spiral track. The rotation of the disc would be in the counterclockwise direction (as seen from the side of the reading laser), and the spiral track would be in the clockwise direction. Given that the pit 20 direction can be reversed without changing the electrical signal seen by the player, in another embodiment of the current invention the pits 20 are molded as depressions 500 into the L1 substrate 420, by employing a normal (father/son) DVD-5 stamper 30/45, as illustrated in FIG. 14. The direction of the spiral track is reversed during mastering, as the disc will be read from the side of the bonding layer 401, rather than through the substrate as in a standard DVD-5. The resulting disc has information encoded as a DVD-5, although the pits 20 are formed in the L1 layer 420: the surfaces of the pits 20 are above the surfaces of the lands 25, and the lands 25 are at the reference plane of the L1 layer 420, as illustrated in FIG. 15. The pit 20 width, length, height, and shape give the corresponding HF signals needed to decode the data on the DVD. The signals are encoded utilizing an eight-to-fourteen modulation (EFM) signal. The pit 20 edges and slopes of the sidewalls serve to distinguish the logical transition of 0's and 1's. This results in pit 20 length units measured as 3 units long to 14 units long, which set the frequency limits of the EFM signal, read from the disc. This measurement is commonly referred to as 3T-14T signal with T referring to a period of time. As long, as the pits 20 are replicated in standard fashion, the player will still be able to distinguish the pit 20 start and end position, while reading from the reverse side, to correctly identify its data identity. In many circumstances this will be the preferred embodiment of the invention, as it does not require molding from the mother stamper 40, as is the case with Special DVD-5 design #1 above.

The actual height of the pits 20 in a standard DVD-5 is typically somewhat less than one quarter wavelength of the reading laser. This is intended to avoid complete cancellation of the reflected laser during a pit-to-land transition, which facilitates the functioning of player electronics. For example, a value of 0.88*(laser wavelength)/4 is sometimes recommended, i.e. approximately 90 nanometers for a material with RI=1.55. Thus it may be desirable to mold the pit 20 surfaces in this embodiment of the current invention somewhat higher than one quarter the wavelength of the reading laser, so that the change in the path of the reading laser during a transition from a land 25 to a pit 20 in the special DVD-5 design #2 will be exactly one wavelength longer than the corresponding change in a standard DVD-5. For example, if the reading laser wavelength is 650 nanometers (i.e., 420 nm in a polycarbonate substrate of RI=1.55), and the pits in a standard DVD-5 are 90 nanometers, the pits 20 in this embodiment (Special DVD-5 design #2) can be molded at 120 nanometers, i.e., one half wavelength (210 nm) from the position of the pit 20 surface in design #1.

EXAMPLE 2

Special DVD-5 Design #2

A special stamper for molding L1 substrates 420 for Special DVD-5 Design #2 was produced through a modified mastering process, where the direction of rotation of the laser beam recorder turntable was reversed during the cutting process, resulting in a spiral tracking path in the opposite direction from that in a normal DVD-5. This stamper was produced by forcing the turntable to rotate in the reverse direction from cutting a normal DVD-5, while the content information was fed to the laser beam recorder as a DVD-5 image. The scanning velocity that is normally preset for DVD formats was manually set to the velocity of 3.49 m/s typical in DVD-5 mastering. L1 substrates 420 were then molded on standard molding machines set up for DVD-5 fabrication.

Some of the molded L1 substrates 420 were bonded using optical grade UV curable DVD adhesives to blank L0 substrates 415, to manufacture design #2 of the Special DVD-5. As in Example 1, the L0 substrates 415 were molded at a thickness of 0.55~0.57 mm (i.e., 30~50 micron thinner than standard DVD halves) to compensate for the bonding layer 401 in the optical path, thus preserving the same focal depth for the information-carrying layer as in a standard DVD-5. To bond the discs, the machines were placed into a DVD-9 production mode and the semi-reflective metallizer for the L0 layer was taken offline. Then the cure time was adjusted to compensate for the decrease in cure exposure needed due to the missing semi-reflective layer. Curing was basically set for a DVD-5 disc, and the disc was flipped to cure through the L0 layer. This function is typically reserved for DVD-9 production.

Figure 22:
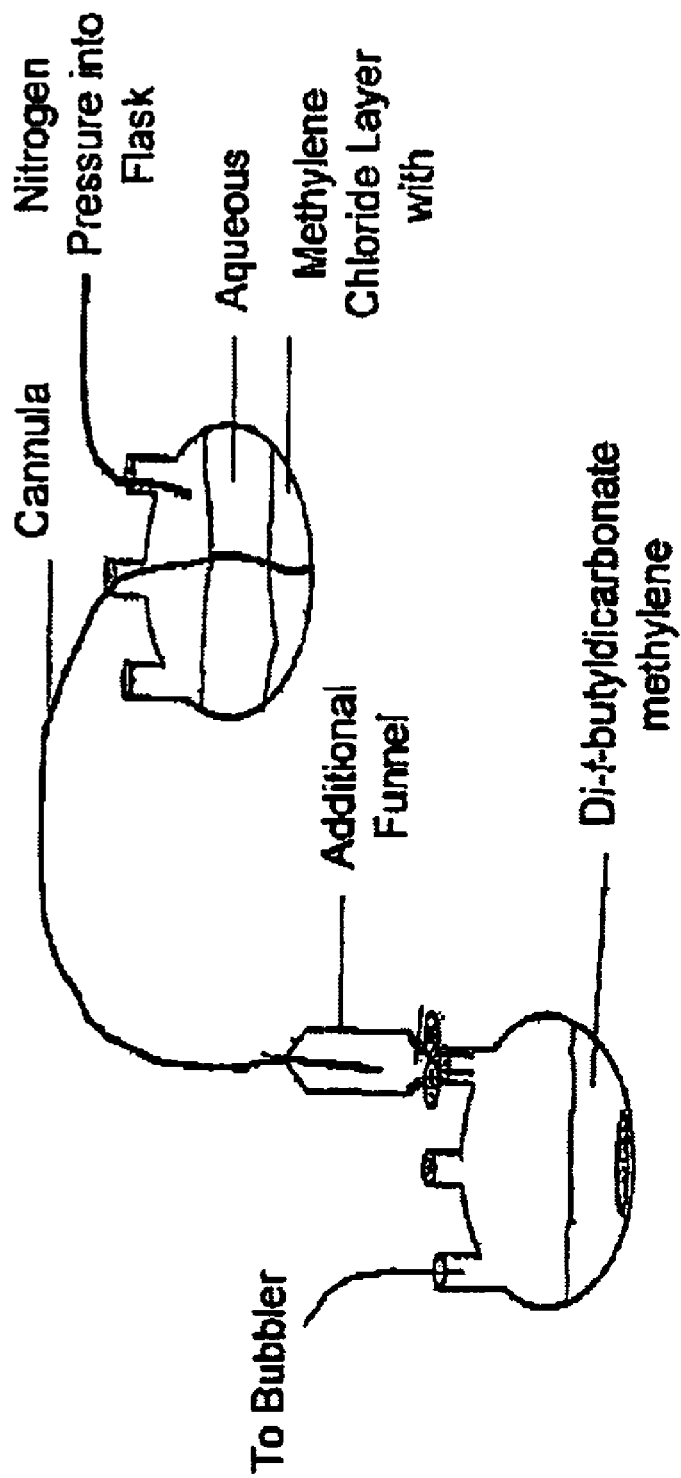
FIG. 22 illustrates the transfer of a methylene chloride solution, done in two portions, into a nitrogen filled 12-liter flask equipped with an overhead stirrer consistent with the present invention.

The discs were then tested with a Koch DVD testing system and played in four different DVD players. They performed indistinguishably from regular DVD-5 discs, as illustrated in FIGS. 21 and 22. Also, the discs played with no errors in an additional three DVD players and two DVD-ROM drives.

Some of the molded substrates were used to manufacture discs with a reactive bonding layer (see Example 9).

Special DVD-5 Design #3

Figure 16:
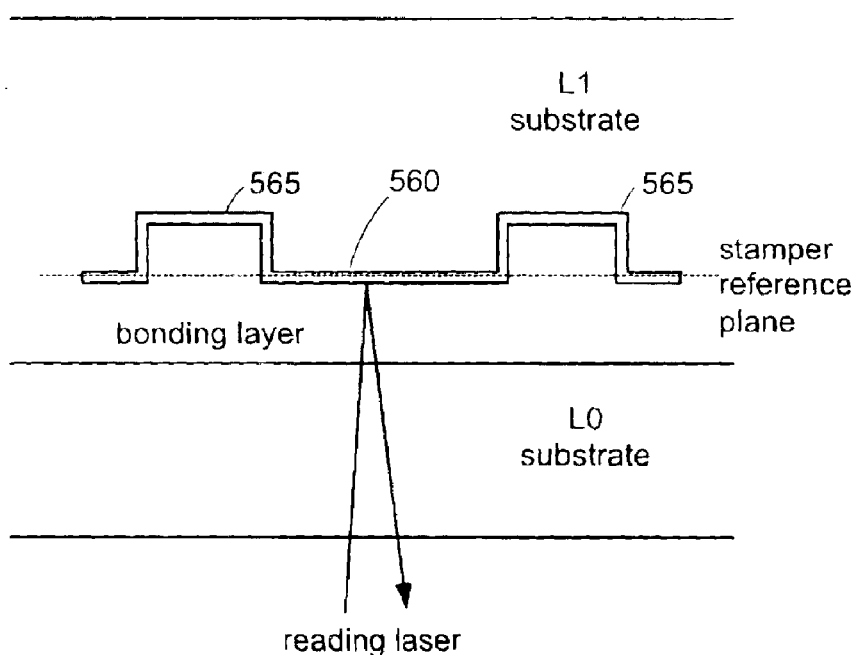
FIG. 16 is a schematic cross sectional view illustrating the stamper reference plane of a modified DVD-5 construct wherein the pits are above the reference plane of the L1 substrate and the lands are at the reference plane of the L1 substrate.

The electronics of optical media drives, including DVD players, can be designed to read the information contained in a layer on the disc by identifying pits 20 and lands 25 in that layer based on the absolute and/or relative elevation of these pits 20 and lands 25, thus distinguishing between an "up" and a "down" transition in the information encoding layer, but without being influenced by the elevation of the pits 20 and lands 25 relative to the reference plane 450 of the layer. Thus in another embodiment of the current invention, during mastering the direction of the spiral track is reversed and also the pits 20 and lands 25 are reversed, so that the pits 20 become lands 25 on the resulting stamper 30, and lands 25 become pits 555. The L1 substrate 420 is then molded by employing 550 a normal (father) stamper 30 and is bonded to a blank L0 substrate 415. The resulting disc has information encoded as a DVD-5, the relative elevation of pits and lands, and the "up" and "down" transitions in the information encoding layer, are identical to a DVD-5. Specifically, the surface of the pits is below the surface of the lands. However, while in a standard DVD-5 the surface of the lands is at the reference plane of the L0 layer, in this embodiment it is the surface of the lands 560 (corresponding to pits on a standard DVD-5) that is at the reference plane of the L1 layer, with the pits 565 (corresponding to lands on a regular DVD-5) being above this reference plane, as illustrated in FIG. 16.

The Reactive Bonding Layer

Another embodiment of the present invention is having a reactive material incorporated in an interstitial layer. In one embodiment, the interstitial layer is the bonding layer of the disc.

In one embodiment of the invention, the stimulus triggering the reaction is exposure to atmospheric oxygen. Upon exposure to oxygen, a reactive material, e.g., leuco methylene blue, which is essentially colorless, is oxidized to form an opaque or semi-opaque layer (e.g., the deep blue dye, methylene blue). Data storage media with the opaque/semi-opaque layer can no longer be played in media players. By adjusting the time it takes to turn opaque, this method can be used to provide limited-play data storage media having the desired life for the given application.

The reactive layer, which comprises both a carrier and a reactive material, should initially have sufficient transmission to enable data retrieval by the data storage media device, and subsequently form a layer which inhibits data retrieval by that device (e.g., which absorbs a sufficient amount of light i.e., incident and/or reflected light) at the wavelength of the laser in the given device). Typically a layer that allows an initial percent reflectivity from the reflective layer of about 50% or greater can be employed, with an initial percent reflectivity of about 65% or greater preferred, and an initial percent reflection of about 75% or greater more preferred. Once the media has been exposed to oxygen, e.g., air, for a desired period of time (e.g., the desired allowable play time of the media), the layer preferably comprises a percent reflectivity of about 45% or less, with about 30% or less preferred, about 20% or less more preferred, and about 15% or less especially preferred.

Possible reactive materials include, but are not limited to, oxygen sensitive leuco or reduced forms of phenothiazines, phenoxazines, and phenazines, whose members include: Methylene Blue, Brilliant Cresyl Blue, Basic Blue 3, Methylene Green, Taylor's Blue, Meldola's Blue, New Methylene Blue, Thionin, Nile Blue, Celestine Blue, and Toluidine 0, as well as reaction products and combinations comprising at least one of the foregoing material; the structures of which are set forth below:

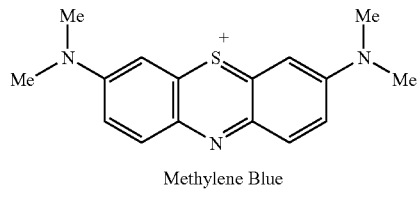

Methylene Blue
661 nm

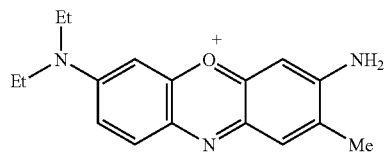

Brilliant Cresyl Blue
622 nm

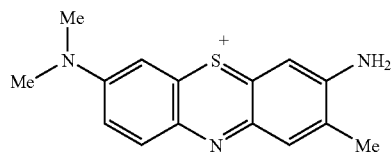

Toluidine Blue O
626 nm

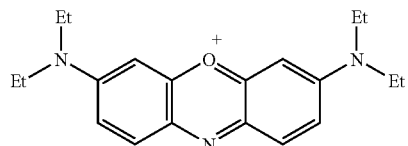

Basic Blue 3
654 nm

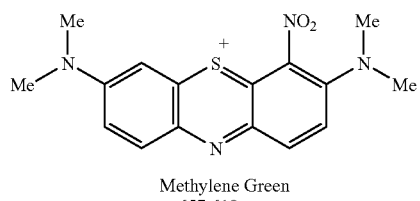

Methylene Green
657,618 nm

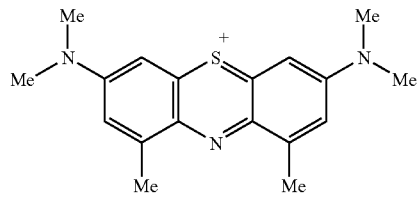

Taylor's Blue
649 nm

-continued

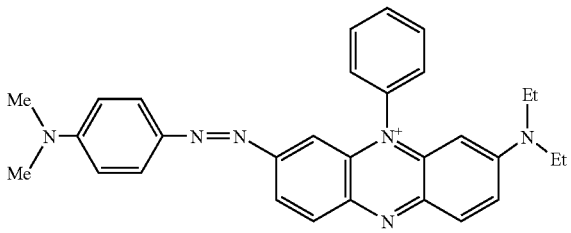

Janus Green B
660,395 nm

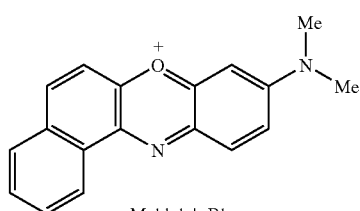

Meldola's Blue
570 nm

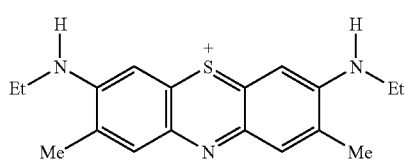

New Methylene Blue
630,591 nm

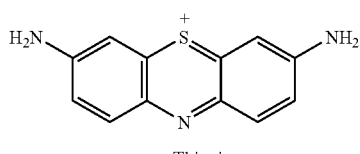

Thionin
598 nm

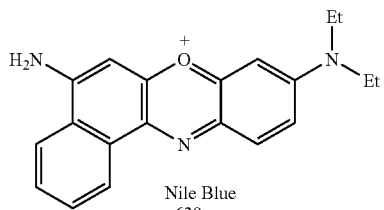

Nile Blue
638 nm

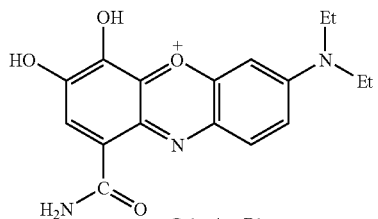

Celestine Blue
642 nm

A method of synthesis of leucomethylene blue and the oxygen dependent reoxidation to form the colored form of the methylene blue dye is shown below:

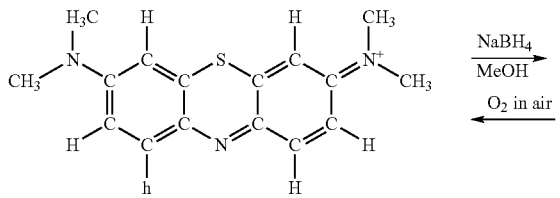 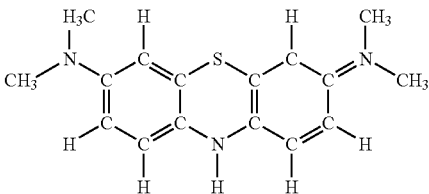

In addition to the above reactive materials, numerous other dyes and light blocking materials, can be synthesized to operate to render the data storage media limited play. For example, some other possible reactive materials can be found in U.S. Pat. No. 4,404,257, hereafter incorporated by reference, and U.S. Pat. No. 5,815,484, hereafter incorporated by reference. Additional examples include.

(a) leuco-azine dyes, such as those disclosed in U.S. Pat. No. 4,710,570, herein incorporated by reference in its entirety

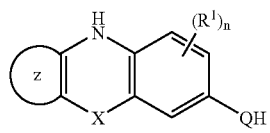

in which:

X is O, S, $NR_2$

Z completes a fused aromatic or hetercyclic ring system

N is 0 or 1 to allow one $R^1$ ring substituent

Q represents $CR_4R_5$ in which at least one of $R_4$ and $R_5$ is an electronegative group or $R_4$ and $R_5$ may complete a ring, or when X is S, Q may represent $NR_3$ in which $R_3$ is an aromatic or heterocyclic group.

(b) quinoneimines, including indamines, indophenols, and indoanilines, such as those disclosed in U.S. Pat. No. 5,424,475, herein incorporated by reference in its entirety and for example, include the following:

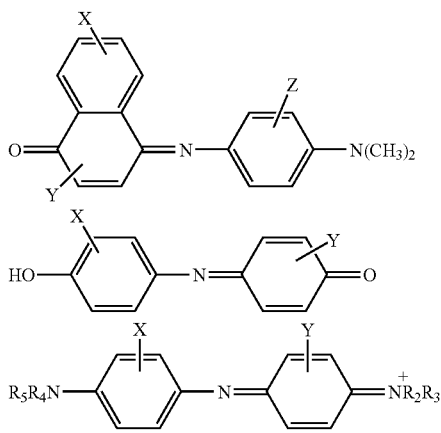

where X, Y, and Z can be but are not limited to: hydrogen, alkyl, alkoxy, aryl, substituted alkyl, alkoxy, and aryl, OH, CN, halogens, $NR_6R_7$, $SR_8$, $SO_2R_9$ where $R_2$–$R_9$ may be hydrogen alkyl, aryl, substituted alkyl or aryl, or may represent the atoms necessary to complete an aromatic or acyclic ring system which may contain heteroatoms and substitution.

(c) anthraquinones; and include, for example,

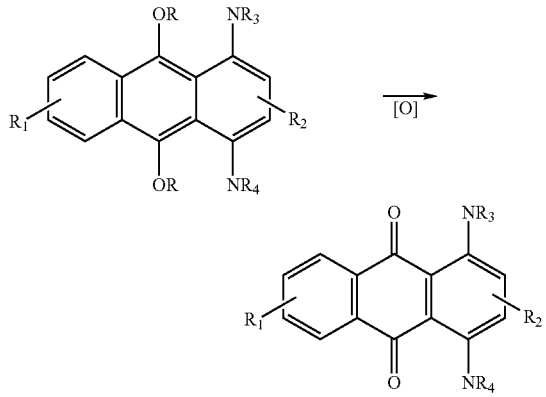

where $R_1$ and $R_2$ can be but are not limited to: hydrogen, alkyl, alkoxy, aryl, substituted alkyl, alkoxy, and aryl, OH, CN, halogens, $NR_5R_6$, $SR_7$, $SO_2R_8$ where $R_5$–$R_8$ may be hydrogen, alkyl, aryl, substituted alkyl or aryl, or may represent the atoms necessary to complete an aromatic or acyclic ring system which may contain heteroatoms and substitution.

(d) acridinies; and include, for example,

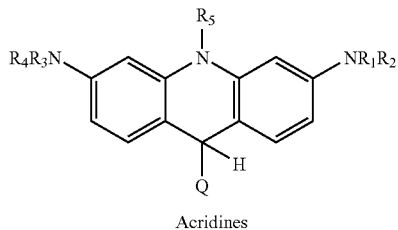

Acridines where $R_1$–$R_4$ call be but are not limited to: hydrogen, alkyl, aryl, substituted alkyl or aryl, or may represent the atoms necessary to complete an aromatic or acyclic ring system which may contain heteroatoms with substitution, and $R_5$ can be but is not limited to: hydrogen, alkyl, aryl, substituted alkyl and aryl groups.

(e) and di- and triarylmethane dyes, such as those disclosed in U.S. Pat. No. 5,330,864 and herein incorporated by reference in its entirety and include for example,

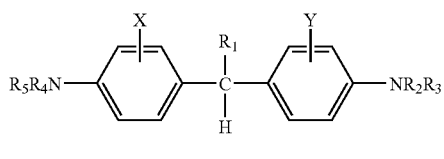

Triaryl methane when $R_1$ = aryl where X and Y can be but are not limited to: hydrogen, alkyl, alkoxy, aryl, substituted alkyl, alkoxy, and aryl, OH, CN, halogens, $NR_6R_7$, $SR_8$, $SO_2R_9$ where $R_2$–$R_7$ may be hydrogen alkyl, aryl, substituted alkyl or aryl, or may represent the atoms necessary to complete all aromatic or acyclic ring system which may contain heteroatoms and substitution. It is understood that R1 can be a substituted aryl.

Additional reactive materials include, but are not limited to, pH indicator materials, materials that undergo photopolymerization, materials that produce precipitates, and light activated chemistries.

The reactive materials can further comprise a mixture comprising at least one of any of the above mentioned reactive materials.

In one embodiment of the present invention, the reactive material is mixed with a carrier for deposition on and/or impregnation into at least a portion of the surface of the substrate. Possible carriers comprise the thermoplastic acrylic polymers, polyester resins, epoxy resins, polythiolenes, UV curable organic resins, polyurethanes, thermosettable acrylic polymers, alkyds, vinyl resins and the like, as well as combinations comprising at least one of the foregoing carriers. Polyesters include, for example the reaction products of aliphatic dicarboxylic acids including, e.g., fumaric or maleic acid with glycols, such as ethyleneglycol, propyleneglycol, neopentylglycol, and the like, as well as reaction products and mixtures comprising at least one of the foregoing.

Some epoxy resins, which can be the used as the organic resin, include monomeric, dimeric, oligomeric, or polymeric epoxy material containing one or a plurality of epoxy functional groups. For example, reaction products of bis phenol-A and epichlorohydrin, or the epichlorohydrin with phenol-formaldehyde resins, and the like. Other organic resins can be in the form of mixtures of polyolefin and polythiols, such as shown by Kehr et al, U.S. Pat. Nos. 3,697,395 and 3,697,402, hereafter incorporated by reference.

A Non-Bonding Reactive Layer

Optionally, the reactive layer can be applied to the substrate using various coating techniques such as painting, dipping, spraying, spin coating, screen printing, and the like. For example, the reactive layer can be mixed with a relatively volatile solvent, preferably an organic solvent, which is substantially inert towards the polycarbonate, i.e., will not attack and adversely affect the polycarbonate, but which is capable of dissolving the carrier. Examples of some suitable organic solvents include ethylene glycol diacetate, butoxyethanol, the lower alkanols, and the like.

For surface coatings, the reactive layer may also optionally contain various additives such as flatting agents, surface active agents, thixotropic agents, and the like, and reaction products and combinations comprising at least one of the foregoing additives. The thickness of the reactive layer is dependent upon the particular reactive material employed, the concentration thereof in the reactive layer, and the desired absorption characteristics of the layer both initially and after a desired period of time.

Development of Blocked Reactive Compounds

One embodiment of the present invention is the use of blocked forms of the reactive compounds in the reactive layer. These compounds will unblock within a predetermined time period after the disc is manufactured or packaged, and typically before the disc is used by the consumer. This is desirable when the stimulus that triggers the reaction that causes the disc to become unplayable (e.g., atmospheric oxygen) can trigger this reaction during the manufacturing of the disc, and thus measures need to be taken so that the reactive compound is not activated during the manufacturing of the disc. For example, in the case of oxygen triggered reactions, unless a blocked form of the reactive compound is used, manufacturing may need to take place in an oxygen free environment, such as a nitrogen atmosphere.

One embodiment of the present invention comprises the use of a chemically blocked and/or modified and/or protected reactive substance(s) for the purpose of producing optical discs that become unplayable after being exposed to a triggering stimulus and/or stimuli (e.g., oxygen, pH change). Specific exemplary blocked dyes and methods of preparing dye precursors are disclosed. Leuco dye precursors which permit the deblocking and oxidation of the leuco dye precursors at acceptable rates and methods of applying dyes and dye precursors to optical discs both on the surface of optical discs and as bonding layers for optical discs are disclosed. Also disclosed is the use of bases to increase the rate of methylene blue generation in blocked leuco dye-containing layers in or on optical discs, and the use of silyating agents such as hexamethyldisilazane to stabilize the blocked leuco dye in coating fluids.

In one embodiment of the invention, to manufacture an optical disc that becomes unplayable after being removed from its package (a "limited-play disc"), the disc incorporates a reactive layer with a composition containing a leuco dye which oxidizes to a colored dye which absorbs light at the wavelength of the reading laser of an optical disc player, preventing enough of the reading laser light from being reflected off the disc to render the disc unplayable. The oxidation of the leuco dye can be initiated by exposure of the coating containing the dye to atmospheric oxygen, which diffuses through the coating to oxidize the leuco dye molecules. One problem with putting such a coating on the surface of the disc is the possibility of the coating being removed by a consumer to make the disc permanently playable. Another problem with putting such a coating on the surface of an optical disc is that this requires an additional step in the disc manufacturing process, entailing higher cost, special tooling for production equipment, and inevitably lower manufacturing yields. Finally, the oxygen-sensitive fluid used to make such a coating is difficult to handle because of its oxygen sensitivity.

In some methods of coating a leuco-dye-containing fluid on the surface of an optical disc, some of which were described above, the coating is solvent based and the solvent must evaporate to yield a hard coat containing the leuco dye and any other components required, typically bound in a polymer matrix. There are several disadvantages to such a solvent coating. First, most of the solvent based fluid is spun off of the disc during a spin coating manufacturing process and is difficult or impossible to recover due to solvent evaporation, which both wastes fluid (increasing the cost of the process) and fouls the coating equipment. Second, evaporation of the solvent takes time, which reduces the rate at which such coated discs can be manufactured and thereby increases the cost of the process. Third, the solvent vapors emitted by the coated disc during the coating and drying process must be vented from the manufacturing equipment, increasing the cost of the installed equipment and presenting process and environmental obstacles to disc replicators considering adopting this manufacturing process.

All of the problems discussed in the previous two paragraphs could be avoided if the leuco dye could be coated in a solventless, light or radiation cured (hereafter called generically "UV-cured") layer, and if this layer could be the same as the optical disc bonding layer that is used to bond the two substrates which compose certain types of optical disc, such as a DVD. The major obstacle to creating such a system is that many leuco dyes, and in particular leucomethylene blue (hereafter "LMB", which has been used by the present inventors to render DVDs unplayable in a solvent-based, surface coated system), inhibit both radical and cationic polymerization reactions of the type used to cure UV-curable monomers such as the acrylates that are commonly used as adhesives for bonding DVD substrates. The oxidized dyes (including methylene blue) also are inhibitors of such polymerization reactions. So putting a leuco dye (which will inevitably contain some of the oxidized, colored dye) in a UV-curable composition will either prevent the UV-curing from taking place, or slow the UV-curing and make the process much less economical by reducing the rate at which discs can be manufactured. Moreover, the process of UV-curing can result in some of the leuco dye becoming oxidized if any oxygen or other oxidizing agent is present in the layer to be cured, resulting in a product prematurely containing oxidized dye which may interfere with the readability of the disc or change the rate at which it becomes unreadable after exposure to oxygen.

Chemically blocked (sometimes called "protected" and/or "modified") leuco dyes (also called "leuco dye precursors") are known and have been used for decades in applications such as "carbonless copy paper". In particular, blocked versions of leucomethylene blue are known and have been used in such applications, and one such compound at least, benzoyl-leucomethylene blue (BLMB), is commercially available. However, we have found that BLMB does not deblock easily enough to yield an acceptable limited play DVD product. Other blocked leucomethylene blue compounds share this problem, or deblock too easily such that oxidizable leucomethylene blue is generated in the coating fluid before it is desired.

Figure 17:
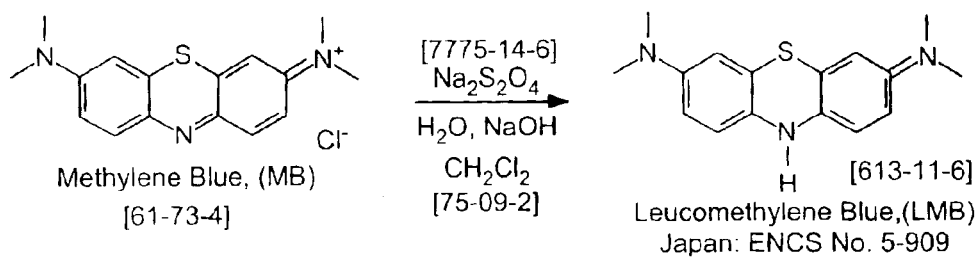
FIG. 17 illustrates a potential synthetic pathway for the synthesis of triisopropylsilyloxycarbonylleucomethylene blue.
Figure 17:
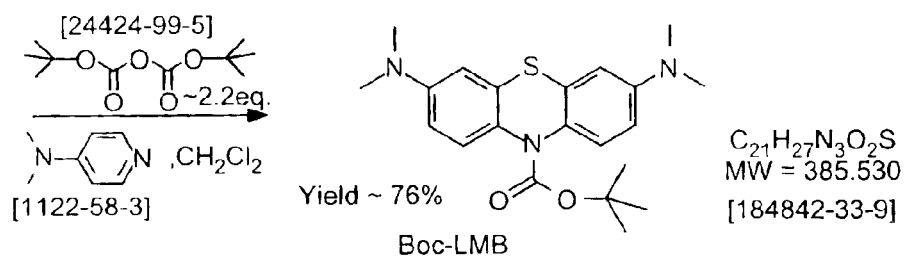
Figure 17:
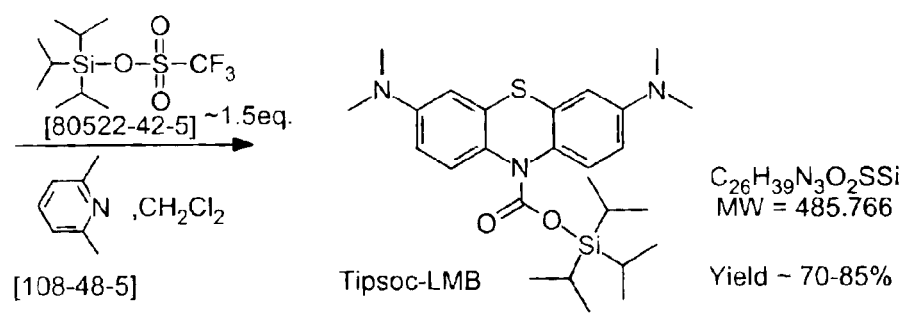

We have found that triisopropylsilyloxycarbonylleucomethylene blue (hereafter "TIPSOCLMB"), whose structure and exemplary synthesis are illustrated in FIG. 17 and described in Example 4, has the following desirable properties for use in creating limited-play DVDs:

1. It is readily synthesized in two steps from commercially available starting materials. By isolating and purifying the BOC-LMB produced in the first step as shown in FIG. 17, the TIPSOCLMB is prepared from a pure compound rather than from the typically very impure methylene blue.
2. It can be incorporated into an acrylate formulation described in Example 5 in which it is stable (to conversion to oxidized methylene blue) for at least several weeks at temperatures below 0 C, allowing coating formulations to be prepared at one facility and shipped to another facility for DVD manufacturing if desired.
3. It can be deblocked in a period of a week or less, presumably by a hydrolysis reaction involving water or other nucleophiles which can either be provided in the acrylate formulation or be absorbed from the atmosphere in which the DVD is manufactured or in the DVD packaging material. Nucleophiles that have shown utility for deblocking are fluoride ion and carboxylate ion, both of which can deblock under essentially neutral pH conditions.
4. The deblocked LMB is stable (to oxidation to methylene blue) in the absence of oxygen. The rate at which the deblocked LMB oxidizes in the presence of oxygen call be controlled by regulating the effective pH of the coating formulation. It is known in the art that the rate of oxidation of LMB increases as the pH of its environment increases. Thus the rate of oxidation can be increased by the addition of basic substances that are soluble in the matrix containing deblocked or blocked LMB and which do not react with the matrix or substrate used. One such basic compound is DABCO (1,4-diazabicyclo[2.2.2]octane), an amine. Other amines may be added or substituted. Further, the addition of a strong protic acid Such as camphorsulfonic acid decreases the rate of LMB oxidation in a polymer film.
5. In the absence of water or other nucleophiles, it is a stable solid which can be stored after synthesis for at least several months, even in the presence of oxygen. Acrylate-based coating fluids containing TIPSOCLMB can be handled in the presence of oxygen until the deblocking reaction has taken place, which reaction is slow enough that the handling of the coating fluid during the DVD manufacturing process can be done in normal (undried) air and is not difficult.

EXAMPLE 3

BocLMB Preparation

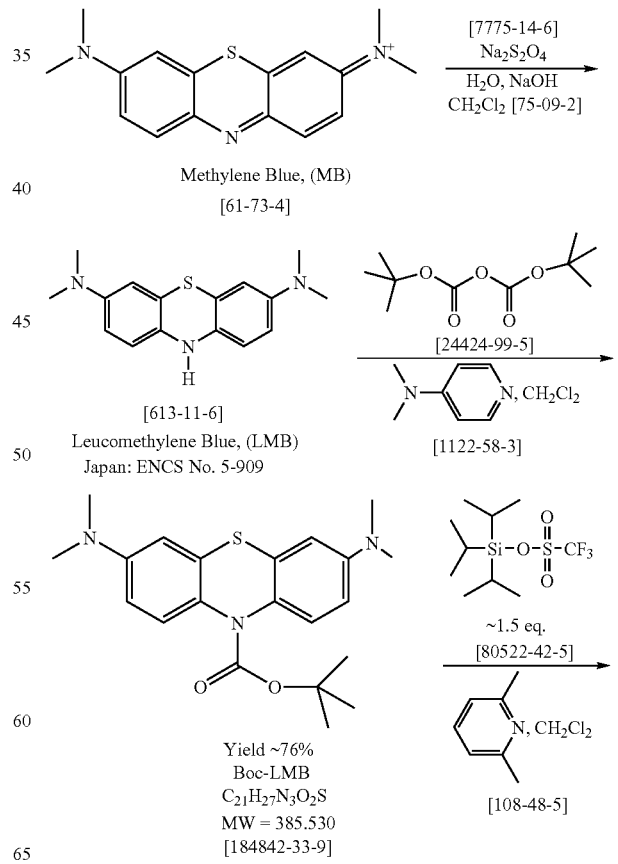

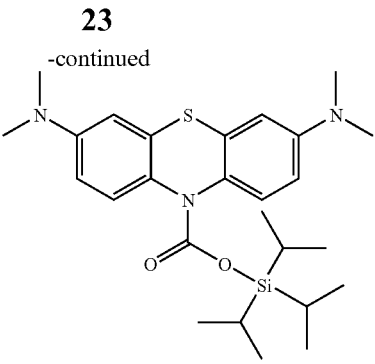

Tipsoc-LMB
Yield ~70–85%
$C_{26}H_{39}N_3O_2SSi$
MW = 485.766 t-BOC-LMB: To 3.6 L of de-ionized water in a 22 liter flask was added 600 grams of methylene blue trihydrate which was dissolved by stirring. Solution dithionite (sodium hydrosulfite), 600 grams, was added to the stirred solution that was blanketed by nitrogen. Over the course of 10 minutes was added 2.4 L of 10% sodium hydroxide solution followed by 9.6 L of methylene chloride. The tip speed of the blade should be 130–150 ft/min; stirring too rapidly affords excessive rag layer/emulsion. The solution was stirred for 30 minutes. After stirring for 30 minutes, the layers were allowed to separate. The leuco methylene blue/methylene chloride layer was pressure transferred with $N_2$ to a 4 L separatory funnel, which was also equipped with a $N_2$ bubbler. The Transfer was done in two portions, allowing time for the layers to separate. The methylene chloride solution was transferred into a nitrogen filled 12-liter flask equipped with an overhead stirrer, as shown in FIG. 22.

When the methylene chloride solution had been completely transferred to the flask, 30 grams of 4-dimethylaminopyridine were added to the solution. The separatory funnel was replaced with an addition funnel containing 770 g of di-t-butyl-dicarbonate that was then added dropwise to the LMB methylene chloride solution, and the solution was stirred overnight at ambient temperature. Care was taken to blanket the leuco methylene blue solution with nitrogen during each step of the process. About 95+% of the methylene chloride was removed by distillation at which time ~9 liters of heptane were added. Distillation was continued until the distillate temperature reached 52° C. The resulting blue-gray solid was filtered and washed with 3 L of heptane and then 3 L of methanol to afford 360 g (58% yield) of t-BOC-LMB.

Methylene Blue (Tipsoc-LMB)

Tipsoc-LMB Synthesis Including Likely Byproducts

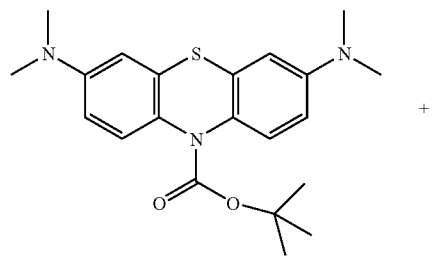

Boc-LMB [184842-33-9]

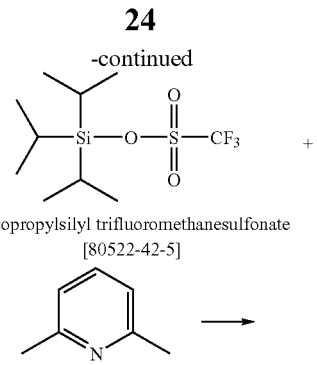

Triisopropylsilyl trifluoromethanesulfonate
[80522-42-5]

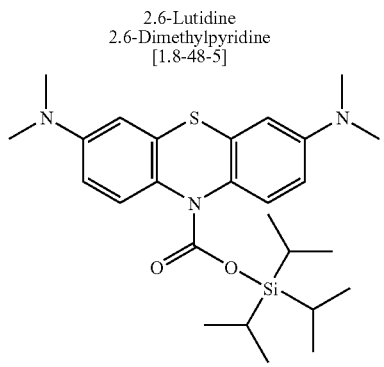

2.6-Lutidine
2.6-Dimethylpyridine
[1.8-48-5]

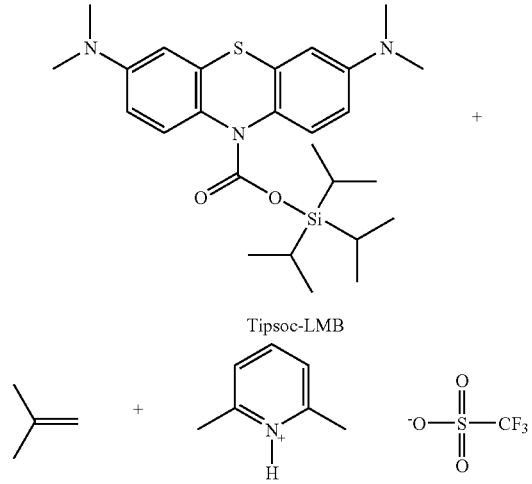

Tipsoc-LMB

Isobutylene =
2-Methylpropene
[115-11-7]
or poly(isobutylene)
[9003-27-4]

2.6-Lutidinium trifluromethanesulfonate
2.6-Dimethylpyridinium trifluoromethanesulfonat
[119503-59-2]

$CH_2Cl_2$ (methylene chloride, dicloromethane, [75-09-2])
is used as the reaction solvent. Hexane [110-54-3] or
Hexanes [73513-42-5] are used
in the workup.

Tipsoc-LMB: In a 12-L, 3-necked, round-bottomed flask equipped with an overhead stirrer, addition funnel, condenser, and a nitrogen bubbler, was dissolved 360 g t-BOC-LMB in 2.5 L methylene chloride to give a bluish solution. To this solution was added 240 g of 2,6-lutidine, followed by dropwise addition of 430 g of triisopropylsilyl trifluoromethanesulfonate (TipsOTf) over 1 hour. The greenish-blue reaction mixture was then stirred under reflux 6 hours and allowed to stir at ambient temperature overnight.

The solution was then concentrated on a rotary evaporator under vacuum to remove most of the methylene chloride, resulting in a dark green-blue mixture. This mixture was split in two portions and each portion was added to 3 L of hot heptane. It is desirable to keep water out of the heptane in this step and all subsequent steps. Each was stirred until a deep blue residue separated from the hot heptane solution containing Tipsoc-LMB. The hot heptane solution was decanted from the residue and allowed to cool in a $N_2$ bag for 48-hour period before filtering. The product was filtered under a $N_2$ blanket, it is desirable to minimize moisture exposure, and dried in a nitrogen bag to yield 268 g of a first crop of Tipsoc-LMB.

The Tipsoc-LMB was recrystallized by dissolving the 268 grams of Tipsoc-LMB in 2.5 liters of boiling heptane containing 14 grams of decolorizing carbon, Pac 200 from Norit Americas zinc. In small scale recrystallizations, Calgon AQ-30 granulated carbon has also been effective. The hot heptane solution, which should be essentially colorless, was filtered through a pad of dry Celite and cooled to afford 200 grams of 99.75% pure Tipsoc-LMB, m.p. 118–119.

Figure 18A:
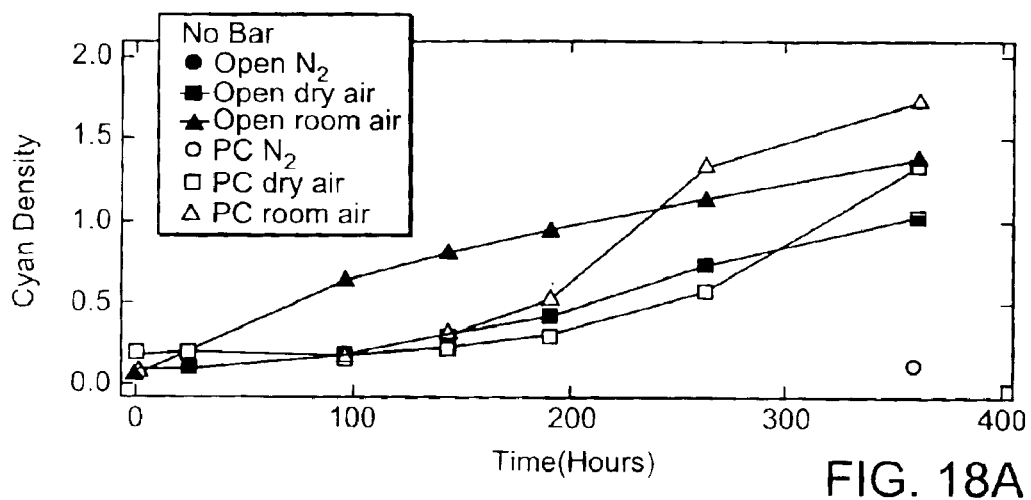
FIG. 18 illustrates the cyan reflectance density of optically readable storage media coated with triisopropylsilyloxycarbonylleucomethylene blue as a function of time in the presence 1,4-diazabicyclo[2,2,2]octane.
Figure 18B:
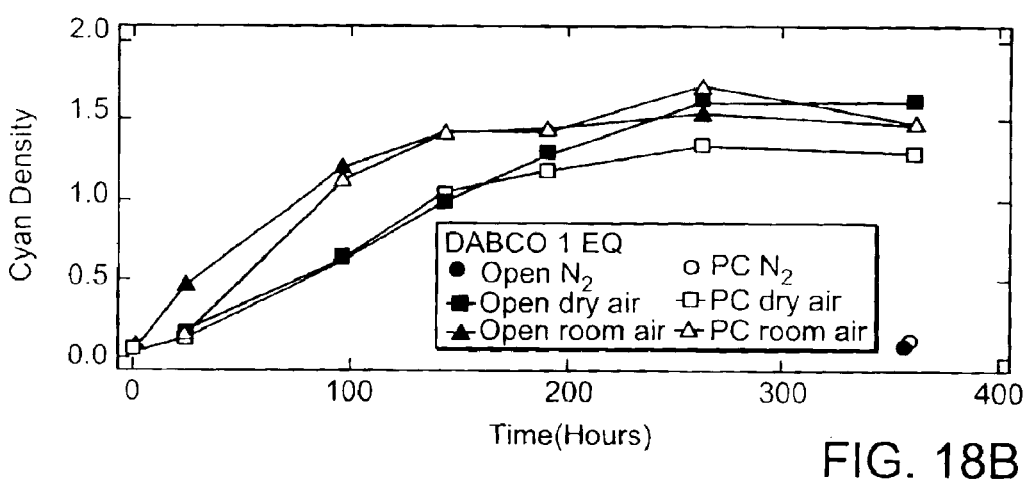
Figure 18C:
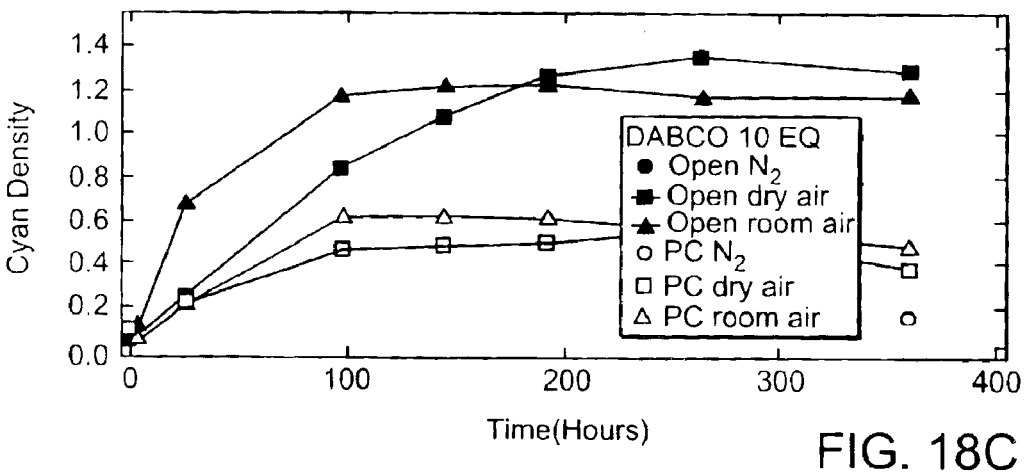
Figure 19:
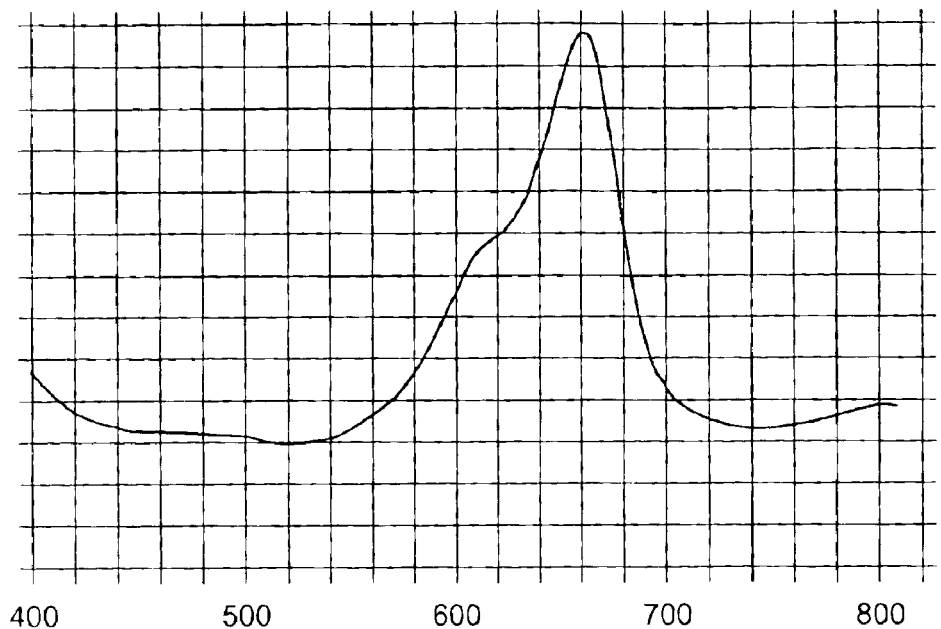
FIG. 19 is a graphic depicting the spectral absorption of methelene blue.

Examples 5 and 6 illustrate how TIPSOCLMB can be incorporated in a coating fluid that can be UV-cured to create a reactive layer containing TIPSOCLMB. Example 7 illustrates how the above technique can produce an interstitial reactive layer, which allows the Special DVD-5 designs 1, 2 and 3 to be used to manufacture expiring optical discs. Example 8 illustrates how TIPSOCLMB deblocks and becomes oxygen sensitive LMB in either a surface or an interstitial layer. When exposed to oxygen, the LMB oxidizes into methylene blue, as illustrated by the increasing cyan density in FIG. 18; methylene blue strongly absorbs light in the 650 nm wavelength, as illustrated in FIG. 19.

EXAMPLE 5

Formulation of Coating Fluid Containing TIPSOCLMB 80 mg TIPSOCLMB
80 mg Irgacure 819 (Ciba Geigy; sensitizer)
4.0 ml CD-501 acrylate (Sartomer; propoxylated[6] trimethylolpropanetriacrylate)
18.5 mg 1,4-diazabicyclo[2.2.2]octane ("Dabco"; Aldrich; base)
155 µl 1,1,1,3,3,3-hexamethyldisilazane ("HMDZ"; Aldrich"; stabilizer)

The TIPSOCLMB, Irgacure 819, and Dabco are weighed into a brown glass bottle, a stir bar is added, the CD-501 is poured in to the proper weight, and the HMDZ is added by syringe. Dry nitrogen is blown into the bottle for a few minutes and the bottle is capped and the cap covered by parafilm. The contents are stirred at room temperature for at least two hours to dissolve the solids. If not all of the material is used, blow the bottle with nitrogen, cap and seal with parafilm, and store in a freezer; warm the bottle before opening to prevent water from condensing in the bottle.

EXAMPLE 6

Preparation of Disk Surface-Coated with TIPSOCLMB/Acrylate Formulation

A DVD clear half disk (an unmetalized 0.6 mm thick and 120 mm diameter polycarbonate disc) or a full DVD (two layers bonded together, back to back with a adhesive) is centered on a laboratory spin coating turntable rotating at roughly 60 rpm's. A 4 ml solution from example #5 is then applied uniformly in a circular ring by a syringe at about a 34 to 40 mm diameter from the center of the disc. The spin speed is then rapidly increased to about 200 rpm for about 15 seconds, resulting in a coating of acrylate/TIPSOCLMB fluid about five µm thick. The spinning is slowed; excess fluid wiped off of the edge of the disk with a tissue and base solvent, if available, and then removed to a lab bench. At this point, the disc is subjected to about five flashes from a Norlite 400 xenon flash lamp at its max setting. The time between flashes is dictated by the charging of the flash lamp, but should be sufficient as to not induce added stress from heat generated in the cure (typically about 5 seconds). This process will yield a clear, uncolored, fully cured acrylate film. Other disks are also prepared with similar acrylate formulations that contain either no Dabco or 10× the amount of Dabco described in Example 5.

EXAMPLE 7

Preparation of Disk Sandwich-Coated with TIPSOCLMB/Acrylate Formulation

A DVD hall disk is centered data side up on the turntable as stated above. The turntable is held stationary while the fluid is dispensed on the data side in a manner creating drops with a syringe roughly 3~5 mm round. These are evenly spaced about 3 mm apart on a diameter of 30~40 mm. The disc to be bonded is then placed data side facing the solution and slightly bowed away from the bottom disc by the edges. The disc will be lowered at angle until the first contact point between a fluid drop and top disc occurs. We do not want to place the top disc immediately on the bottom because of entrapped air and subsequent bubbles. Therefore, to get a more uniform capillary flow, we can rotate the disc in a clockwise rotation while keeping it slightly bent under light pressure until each of the fluid drops begins to form a capillary bridge ring. Once the capillary ring is completed, the top disc can be released and the capillary action will continue. We can wait for the capillary flow to cover the surface, or we can spin the disc at 100 rpm's until the material at least reaches the maximum OD diameter. At this point the turntable can be turned on and rotated at about 500 rpm's for 5 seconds. This will level the spacer layer (adhesive layer) and remove excess material from the OD. The disc edge can then be wiped and the disc will then be UV cured. It is important that prior to curing, the disc halves be aligned as close as possible to avoid center hole misalignment an subsequent play back problems. At this point, the disc is subjected to about 20~30 flashes from a Norlite 400 xenon flash lamp at its max setting. The time between flashes is dictated by the charging of the flash lamp, but should be sufficient as to not induce added stress from heat generated in the cure (Typically 5 seconds). This process will yield a clear, uncolored, fully cured acrylate film. Other disks are prepared with similar acrylate formulations that contain either no Dabco or 10× the amount of Dabco described in Example 5.

EXAMPLE 8

Deblocking and Oxidation of TIPSOCLMB in Surface and Sandwich-Coated Disks, and the Effect of a Base Included in the Coating Formulation Disks prepared as described in Examples 6 and 7 were cut into six 'chips' each and the chips were stored in either dry nitrogen, dry air, or room air (average RH about 30%) and their cyan reflectance densities were recorded periodically with an X-Rite 504 densitometer (the samples stored in nitrogen were only tested at the start and end of the experiment as they were visibly unchanged and it was desired to minimize their exposure to oxygen). In all cases the samples stored in nitrogen showed no methylene blue (MB) generation, as expected. Incorporating 1,4-diazabicyclo [2.2.2]octane (Dabco) into an acrylate formulation at 1.0 equivalent with respect to the TIPSOCLMB gave very significant acceleration of the deblocking/oxidation rate compared to a control (FIG. 18), while a higher concentration of this compound was actually less effective. In general the open samples (those with the TIPSOCLMB layer coated on top of a DVD half without any cover) generated MB only slightly faster than the sandwich structures, indicating that deblocking and oxidation of the LMB is not significantly limited by the transfer of either water or oxygen through an unmetallized 0.6 mm polycarbonate layer. Rather, the deblocking of the TIPSOCLMB is likely to be rate-limiting in these systems. The control samples without any added base shows noticeably faster MB generation in room air than in dry air, suggesting that moisture in the air speeds deblocking in this sample.

Example 9 illustrates how a reactive bonding layer was incorporated into Special DVD-5 Design #2, thus manufacturing a disc that was normally playable like a DVD-5 and subsequently became unplayable.

EXAMPLE 9

Incorporating TIPSOCLMB into a Special DVD-5 Design #2 Bonding Layer

A set of experiments was performed to test whether a formulation containing TIPSOCLMB, Irgacure-819, Dabco, 1,1,1,3,3,3-hexamethyldisilazane (as a fluid stabilizer), and Sartomer CD-501 acrylate monomer could be used as a DVD adhesive to produce playable DVDs. Using the formulation described in Example 5, filtered through a 1.0 µm glass syringe filter, the fluid was syringed onto either clear or metallized Special DVD-5 Design #2 halves manufactured as in Example 2. A DVD half disk is centered data side up on the turntable as stated above. The turntable is held stationary while the fluid is dispensed on the data side in a manner by creating drops with a syringe roughly 3~5 mm round. These are evenly spaced circularly about a diameter of 30~40 mm. The disc to be bonded is then placed data side facing the solution and slightly bowed away from the bottom disc by the edges. The disc will be lowered at an angle until the first contact point between the fluid and top disc occurs. We do not want to place the top disc immediately on the bottom because of entrapped air and subsequent bubbles. Therefore, to get a more uniform capillary flow, we can rotate the disc in a clockwise rotation while keeping it slightly bent under light pressure until each of the fluid drops begins to form a capillary bridge ring. Once the capillary ring is completed, the top disc can be released and the capillary action will continue. We can wait for the capillary flow to cover the surface, or we can spin the disc at 100 rpm until the material reaches the maximum OD diameter. At this point the turntable can be turned up and rotated at about 500 rpm's for 5 seconds to thin out the adhesive and achieve a resulting 50 µm adhesive films (determined by profilometry). This will level the spacer layer (adhesive layer) and remove excess material from the OD. The disc edge can then be wiped and then the disc UV cured. It is important that prior to curing, the disc halves be aligned as close as possible to avoid center hole misalignment an subsequent play back problems. At this point, the disc is subjected to about 20~30 flashes from a Norlite 400 xenon flash lamp at its max setting. The time between flashes is dictated by the charging of the flash lamp, but should be sufficient as to not induce added stress from heat generated in the cure (Typically 5 seconds). This process will yield a clear, uncolored, fully cured acrylate film that plays on the DVD test player.

The discs were manufactured under normal ambient conditions, and were subsequently put in a nitrogen box for 3–4 days, to remove the oxygen dissolved in the substrates (which in this example took all estimated 12–20 hours), and to allow TIPSOCLMB to unblock into LMB (which in this example took 2–3 days).

The Special DVD-5 design #2 discs were subsequently removed from the nitrogen box and were measured for reflectivity at the 650 nm wavelength as a function of time. The discs were clear and playable for 12–16 hours after which time they turned dark blue within 24 hours and became unplayable with reflectivities under 2% at 650 nm.

Multiple-Layer Optical Discs

As seen in the DVD family illustration in FIG. 4, in a dual layer optical disc designed to read multiple layers from one side, the spacer (bonding) layer is in the optical path. In the case of Dual Layer DVDs, the given specification for this spacer layer thickness is 0.055+/−0.015 mm. The thickness of the substrate for a dual layer DVD with optical path bonding is typically 0.55 0~0.641 mm.

Incorporating a reactive compound inhibiting the reading, laser in the bonding layer 800 of either type of dual-layer disc would only inhibit the player from reading the L1 layer 805, as the bonding layer 800 is not in the optical path for reading the L0 layer 810. Furthermore, the metal 815 in the L0 layer 810 might act as a barrier preventing a predetermined stimulus such as moisture or oxygen to permeate to the reactive compound in the bonding layer 800 in a controllable manner.

One method around this potential problem would be as follows. Typically, when a player or a drive begins reading a disc, it looks for the table of contents or information area in the lead-in area for the L0 layer 810 (see FIG. 6). When authoring the disc, it is possible to have the L0 lead-in 820 area contain commands to directly access the L1 layer 805. In order to be able to read the L0 layer 810 to direct the play sequence to the L1 805, we would have to metallize the L0 side 810. This would then possibly interfere with the reactive adhesive material 800 causing unstable or uncontrolled kinetics of reaction that would be dependent on the permeability of the metal layer. One approach around this would be to change the metallizer masking for the L0 semi-reflective layer 800, which is typically run out to 58 mm to 59 mm radius on the disc, to something closer to the lead-in or information data area on the L0.

Figure 20:
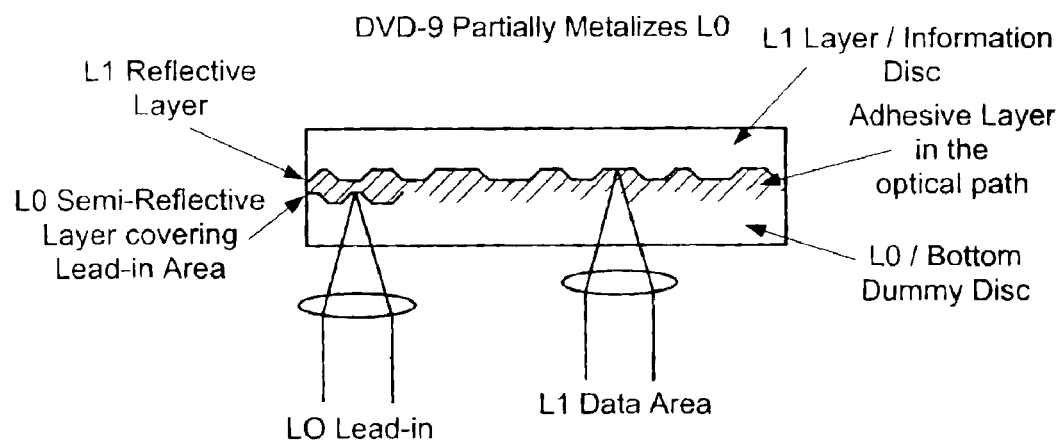
FIG. 20 is a schematic cross sectional view illustrating a modified DVD-9 construct, wherein the L0 layer is partially metallized.
Figures 1, 21A:
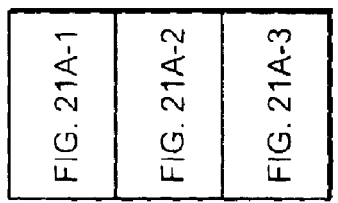
FIGS. 21A and 21B are graphics depicting Koch test results for a modified DVD-5 construct wherein the pits are molded as depressions in the L1 substrate using a father stamper in which the direction of the spiral track is reversed during mastering.
Figures 3, 21A:
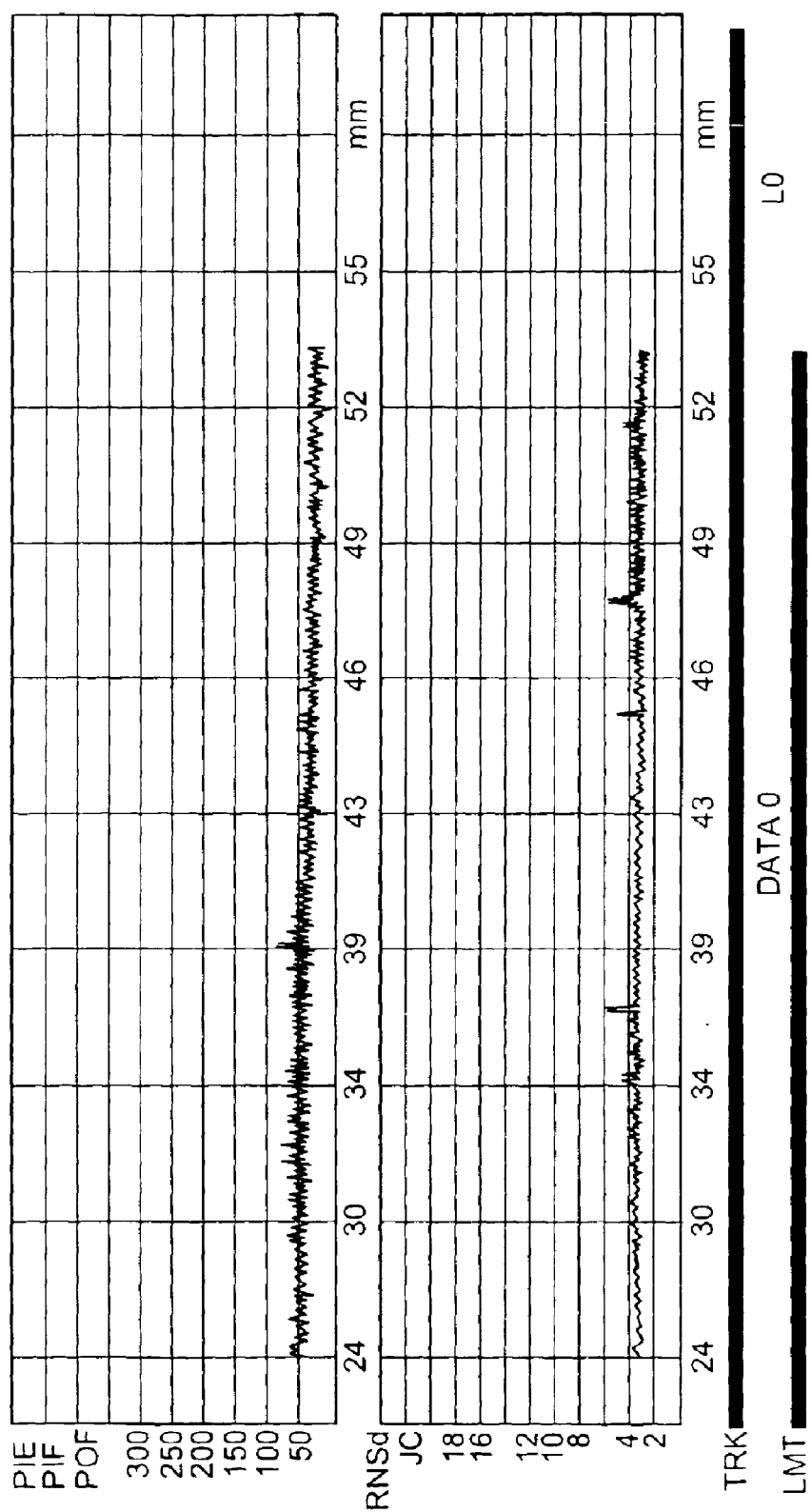
Figures 2, 21B:
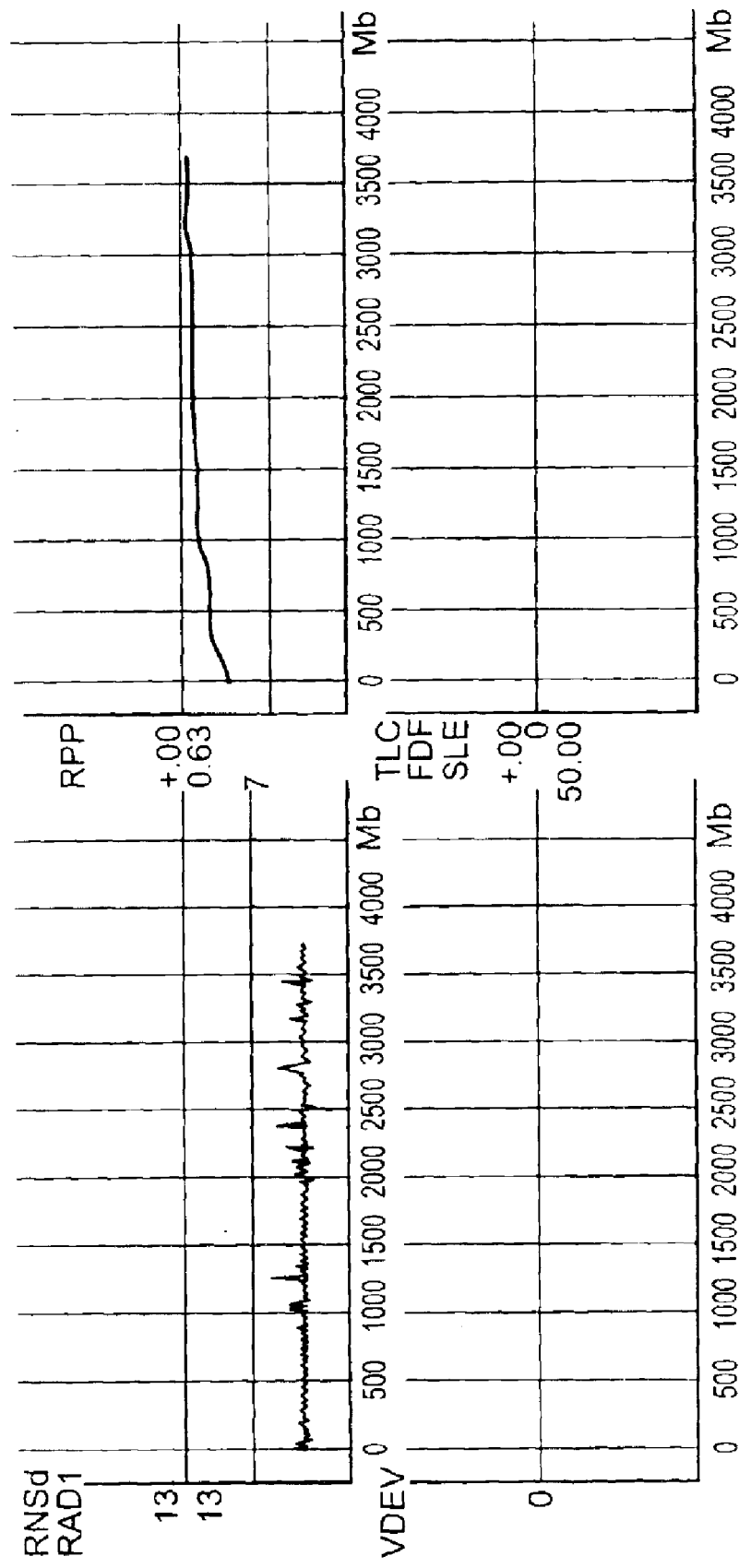
Figures 3, 21B:
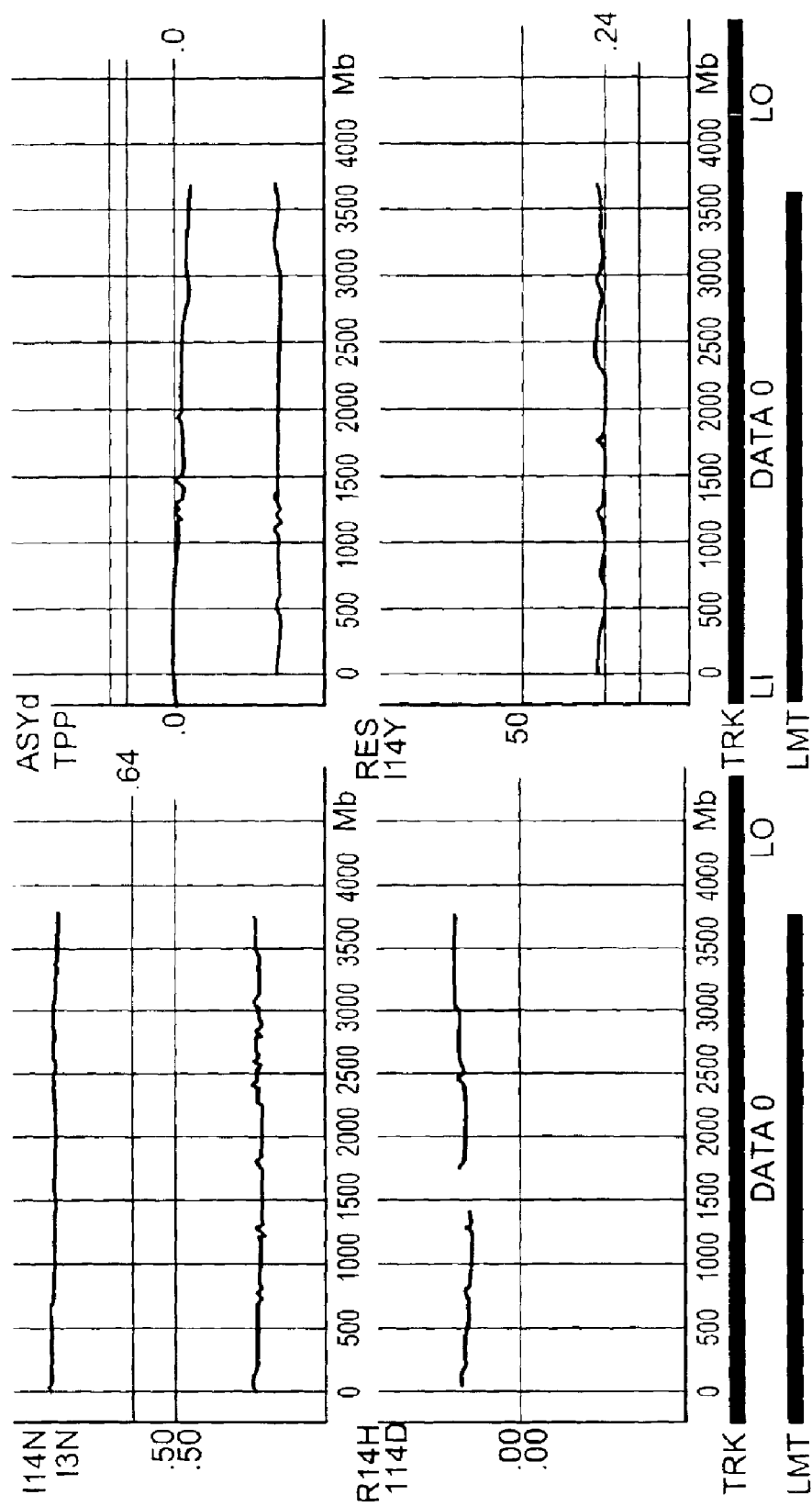

To facilitate activation of the reactive material 800, e.g., when the activating stimulus is oxygen or moisture that might be prevented from reaching the reactive bonding layer 800 because of the L0 metal layer 820, part of the L0 layer 810 can be masked during metallization, so that pelt of the reactive layer will be easier to expose to the stimulus and thus the corresponding part of the L0 layer will be disabled. These discs would have a partially metallized L0 layer 810, as illustrated in FIG. 20. For example, if only the lead-in area or program start portion of the L0 layer 810 is metallized, the player is able to read the lead-in data, and is able to access the information stored on L1 layer 805. As only a small area on the L0 layer 810 would be metallized, a substantial part of the reactive bonding layer would be in direct contact with the L0 substrate 810, which is typically permeable by stimuli such as oxygen or moisture. When the reactive bonding layer responds to the appropriate stimuli and starts interfering with the reading laser, the player is no longer able to access the corresponding part of the L1 layer 805.

Another embodiment of the present invention is utilizing authoring techniques, such as sequencing and branching commands to be executed by the optical media player, to ensure that making a certain part of a disc unplayable will interfere with playing other parts of the disc, or the entire disc. The part of the disc made unplayable for this purpose may be in the single layer of a one-layer disc, or in any of the layers of a multi-layer disc. For example, one embodiment of this invention consists of a DVD-9 authored so that making a certain part of the L1 layer unplayable would interfere with playing other parts of the disc, or the entirety of the disc. For example, reading the L0 layer lead-in area would direct the player to access a part of the L1 layer that would become unreadable when the reactive layer starts interfering with the reading laser, which would cause the disc to be inoperable. A DVD-9 disc can be authored so that all or part of the L1 layer is essential in order to play any information on L0 and/or L1. For example each chapter on the disc can be authored so that it requires reading certain information on L1 before proceeding.

In another embodiment of this invention, activation of the reactive material is facilitated by controlling the deposition of the L0 layer. For example, fast deposition of a gold or silver or silicon L0 layer though sputtering is known to result in grainy dendritic formations that are easier to penetrate by oxygen and moisture. Also, a thinner L0 layer can be deposited, which is easier to penetrate by oxygen and moisture. While depositing grainy or thin L0 layers may be unacceptable for a permanent, archival quality disc, it is often adequate for a limited use, expiring disc.

EXAMPLE 10

DVD-9 Discs with TIPSOCLMB Incorporated in a Reactive Bonding Layer

A DVD-9 with parallel track path encoding can have two distinctly different layers for play back. In the encoding or data mastering process, the Lead-in area normally found on the L0 disc, can have information telling the reading players to read from either or both layers on the disc. Therefore, for this example using a reactive bonding material, the reactive layer could prevent play back from the L1 layer while not affecting the L0. For this example corresponding L0 and L1 masters were manufactured, and L0 and L1 substrates were normally molded and metallized.

The DVD halves were bonded as in example 9 above using an adhesive containing the formulation TIPSOCLMB, Irgacure-819, Dabco, 1,1,1,3,3,3-hexamethyldisilazane (as a fluid stabilizer), and Sartomer CD-501 acrylate monomer described in Example 5. The solution was filtered through a 1.0-µm glass syringe filter. A DVD half disk is centered data side up on the turntable as stated above. The turntable is held stationary while the fluid is dispensed on the data side in a manner by creating drops with a syringe roughly 3~5 mm round. These are evenly spaced circularly about a diameter of 30~40 mm. The disc to be bonded is then placed data side facing the solution and slightly bowed away from the bottom disc by the edges. The disc will be lowered at an angle until the first contact point between the fluid and top disc occurs. We do not want to place the top disc immediately on the bottom because of entrapped air and subsequent bubbles. Therefore, to get a more uniform capillary flow, we can rotate the disc in a clockwise rotation while keeping it slightly bent under light pressure until each of the fluid drops begins to form a capillary bridge ring. Once the capillary ring is completed, the top disc can be released and the capillary action will continue. We can wait for the capillary flow to cover the surface, or we can spin the disc at 100 rpm until the material reaches the maximum OD diameter. At this point the turntable can be turned up and rotated at about 500 rpm's for 5 seconds to thin out the adhesive and achieve a resulting 50 µm adhesive films (determined by profilometry). This will level the spacer layer (adhesive layer) and remove excess material from the OD. The disc edge can then be wiped and then the disc UV cured. It is important that prior to curing, the disc halves be aligned as close as possible to avoid center hole misalignment and subsequent play back problems. At this point, the disc is subjected to about 20~30 flashes from a Norlite 400 xenon flash lamp at its max setting. The time between flashes is dictated by the charging of the flash lamp, but should be sufficient as to not induce added stress from heat generated in the cure (Typically 5 seconds). This process will yield a clear, uncolored, fully cured acrylate film that plays on the DVD test player.

The discs were manufactured under normal ambient conditions, and were subsequently put in a nitrogen box for 7 days, to remove the oxygen dissolved in the substrates (which would take an estimated 12–20 hours), and to allow TIPSOCLMB to unblock into LMB (which was estimated to take up to 5–6 days). The discs were subsequently removed from the nitrogen box and were normally playable on both the L0 and L1 layer for 2–3 (lays on a Pioneer player. After 7 days of exposure to ambient oxygen, the discs became unplayable on the L1 layer, although they would play normally on the L0 layer.

EXAMPLE 11

DVD-9 Discs with Partially Metallized L0 Layer

As in example 10 above, DVD-9 master tapes were generated with the data area being identified on layer L1 and the L0 layer serving only to provide the lead-in and subsequent table of contents relating to the disc type and information. During play back, the L0 lead-in would instruct the disc to read from the L1 data side. In this case, we would not have to metalize the entire surface of the L0 layer because there is no information to be read outside of the lead-in area. Therefore. DVD-9 master tapes were produced with lead-in and command information on L0 and data area on L1. Typically, the metalizer masking covers areas from 25 mm through 118 mm diameters on both layers. Being as the lead-in area data covers the diameters of 25.2 mm to a maximum of 48 mm, and the subsequent information area starts at no less than 48 mm diameter, the metalizer masking can be reduced to cover the lead-in only. This would allow a reflective signal to read the lead-in on the L0 layer and then switch to the L1 layer for data playback without having to read through additional semi-reflective metal.

In this example, we manufactured donut-masking plates that dropped into the metalizer OD mask assembly. By registering the masking from the OD, we are able to reduce the metalized diameter to an area allowing lead-in playback. We extended the mask just outside of the lead-in 48 mm diameter in order to compensate for eccentricity tolerance with the masking position. Additionally, in order to prevent a reflective spike from the transition of clear disc area to metalized disc area when reading the L1 layer, the edge of the masking was slightly raised above the disc to cause a shadowing or tapered layer uniformity. This would cause a gradual focusing compensation rather than a large "speed bump" effect causing its radial noise and focusing error to fall out of specification and perhaps jump track.

The resulting DVD-9 halves were bonded as in Example 10. The DVD-9s constructed were tested for playability in a Pioneer DVD player and in a DVD-ROM drive, and were subsequently put in a nitrogen box for 7 days, so that the TIPSOCLMB would unblock into LMB. The discs were subsequently removed from the nitrogen box and were clear and playable for 12–16 hours, and turned dark blue within 24 hours after that, becoming unplayable. The discs were effectively prevented from having information read from either L0 or L1.

Controlling the Timing of the Reaction

Preferably, the data quality of the disc should remain high for the intended period of use and then decay rapidly resulting in a rapid degradation of the ability to read data off the optical disc. One benefit of this embodiment of the present invention is that for a broad class of stimuli, such as those requiring diffusion of a substance through a barrier layer, incorporating the reactive material in all interstitial layer results in substantial advantages regarding the timing characteristics of the reaction.

One method of achieving the above mentioned desirable timing characteristics is to use a reactive interstitial material between the disc substrates, as described earlier, which reacts with a substance that needs to diffuse through the substrates of the disc. For example, if the reactive material is sensitive to oxygen, there will be an extended period in which there will be no reaction while the oxygen diffuses through the disc substrates. Once oxygen reaches the reactive layer, the resulting reaction can be fast, resulting in rapid expiration of the disc.

When oxygen is used as the diffusing substance, it may be necessary to remove oxygen that dissolves in the disc during the different stages of its manufacture. This can be done, for example, by storing the discs in a vacuum or in an oxygen free environment for an appropriate period of time. It has been established theoretically and experimentally that 24 hours is an adequate period to extricate oxygen dissolved in a 0.6 mm thick polycarbonate disc substrate. Alternatively, if a blocked reactive material is used as described earlier, an oxygen scavenging material, such as iron or an organometallic compound, can be used to extricate oxygen from the optical disc before the blocked reactive material unblocks. This method has several manufacturing advantages; for example, it can avoid oxygen extrication during manufacturing of the disc by including the oxygen scavenging material in the packaging of the disc, which allows the extrication of the oxygen to take place after the disc is manufactured and packaged.

Another means for controlling the timing of the expiration of the disc is to include in or adjacent to the reactive layer a finite, controlled quantity of an appropriate protective substance, such as an antioxidant in the case that the reactive layer reacts with oxygen. The protective substance would prevent the reactions that cause the disc to expire until such time as the anti-oxidant was consumed, at which time the disc would rapidly degrade and become unplayable. For example, an organometallic compound that reacts with oxygen can be packaged with the disc to protect the disc from oxidation while in the package. Alternatively, the organometallic compound can be incorporated into the substrate, thus continuing to protect the metal layer for a period of time alter the package has been opened.

Depletion of a protective substance could be combined with diffusion of the triggering substance through the substrate of the disc, to result in longer delays before the disc expires, or to enable finer control of the characteristics of the expiration process, such as the steepness of reflectivity degradation.

Example of Antioxidant in Reactive Layer

Alternatively, the protective substance may be a reducing agent which may be incorporated into the reactive bonding layer itself. In an experiment in which the concentration of TLMB was also varied and shown to have an effect, the play time was shown to be more greatly affected by varying the amount of stannous ethylhexanoate reducing agent (see Table I).

TABLE I

| Formulation # | Concentration | | Play Time (hrs) | |
|---|---|---|---|---|
| | TLMB | Sn(II) EtHexanoate | short | long |
| A | 1% | 2% | 14 | 22 |
| B | 1% | 4% | 38 | 55 |
| C | 0.5% | 2% | 18 | 26 |
| D | 0.5% | 4% | 46 | 58 |

DVD-5 discs were made using a TIPSOCLMB-containing adhesive formulation, and deblocked in an oxygen-free atmosphere for 48 hours at 60° C. At that time the discs were exposed to ambient room air and the rate of methylene blue color development was quantified with an X-Rite reflection densitometer. The short Play Time was chosen to be the time at which the cyan density increased by 0.35, which roughly corresponds to a playability cutoff at 45% reflectance as typified by a low quality DVD player. The long Play Time was chosen to be the time at which the cyan density increased by 0.85, which roughly corresponds to a playability cutoff at 10% reflectance as typified by a high quality DVD player.

The most likely mechanism for this extended play is reduction of the initially formed methylene blue dye back to the leuco form until most of the reducing agent is consumed. Alternate mechanisms. Such as the stannous compound acting as a primary oxygen scavenger to consume oxygen before the leuco dye is affected, are also possible.

The mobility within the cured matrix is expected to have a significant effect upon the reduction rate; indeed, the calculated glass transition temperature (Tg of the monomers used in this example is $-34°$ C. In such a soft matrix, adequate molecular mobility should exist to allow molecular contact of reducing agent and dye molecules.

Alternate reducing agents might include other Sn(II) compounds which would be soluble in the UV cure formulation, such as acetylacetonate chelates, fatty alpha-aminoacid chelates and salts; soluble iron(II) compounds, such as fatty carboxylates and chelates such as acetylacetonates: ascorbic acid and its derivatives such as ascorbyl palmitate; hydroquinones, such as 2,5-di-tert-amylhydroquinone; alkylhydroxylamines; hydrazines; dithionates with a solubilizing counterion; reducing saccharides such as glucose; alpha-hydroxyketones, such as acetol; appropriately substituted boron and silicon hydrides. Although many of these materials are difficultly soluble in current active adhesive formulations, a more expeditious choice of monomers and oligimers might allow the use of one of these alternate reducing agents while still providing good adhesive and dye stabilization properties.

Preventing Photobleaching of Expired Discs

Polyhydroxystyrenes (for example, PHS-XE-01, available from ChemFirst Electronic Materials L.P, 14785 Preston Road, Suite 480, Dallas, Tex. 75254-912), have been found to be effective photostabilizers for azine dyes in UV cured adhesives. Enhanced photostabilization of azine dyes occurs in formulations in which the selected monomer mixture has a more hydrophobic character. The hydrophobic character may be characterized in this system by alcohol group content; low levels of alcohol groups result in a more hydrophobic matrix compared to higher levels of alcohol. In one experiment, the ratio of monomers (Sartomer SR395, isodecyl acrylate; Sartomer SR495, caprolactone acrylate; and Sartomer SR349, ethoxylated bisphenol A diacrylate)

was varied such that the weight % of SR495 (hydroxy containing monomer) ranged from 39% to 62%. Improved photostability of the methylene blue (produced via in-situ deblocking and oxidation of TIPSOC-LMB) in the respective cured bonding adhesives was found in the formulation with the lower alcohol content.

EXAMPLE A

A series of Part A mixtures was formulated by dissolving polyhydroxystyrene (PHS) into a liquid mixture of varying ratios of two Sartomer monomers, SR495 and SR349 at 60° C. The basic deblocking catalyst, Tinuvin 292, and photoinitiator were added sequentially after all of the PHS had dissolved. The resulting mixtures were stirred until clear mixtures were obtained. The Part B solution was made by dissolving TIPSOC-LMB powder in Sartomer SR395 with slight warming.

|  | Part A Stock Solutions (grams) | | |
| --- | --- | --- | --- |
| Component | I | II | III |
| SR495 | 30.0 | 40.0 | 50.0 |
| SR349 | 30.0 | 20.0 | 10.0 |
| PHS | 9.78 | 9.78 | 9.78 |
| T292 | 0.232 | 0.232 | 0.232 |
| IC819 | 1.60 | 1.60 | 1.60 |

| Component | Part B Stock Solution (grams) |
| --- | --- |
| SR395 | 12.0 |
| TIPSOC-LMB | 0.960 |

The complete active adhesive mixtures were made by adding 0.27 grams of Part B with vigourous shaking to 3.58 grams of each of the three Part A formulations described above. The resulting component ratios of the three formulations is shown in the following chart.

|  | % (wt/wt) | | |
| --- | --- | --- | --- |
| Component | I | II | III |
| SR495 | 39.00 | 51.94 | 64.93 |
| SR349 | 39.00 | 25.97 | 12.98 |
| PHS | 12.70 | 12.7 | 12.7 |
| T292 | 0.30 | 0.3 | 0.3 |
| IC819 | 2.08 | 2.08 | 2.08 |
| SR395 | 6.49 | 6.49 | 6.49 |
| TIPSOC-LMB | 0.52 | 0.52 | 0.52 |

Discs were assembled by spreading 0.6 grams of the full adhesive between two clear LO polycarbonate half discs, and curing the adhesive with a 2 second exposure of a Xenon Corporation DVD xenon flashlamp. The colorless discs were deblocked and oxidized to methylene blue for 24 hours in a 60° C. oven for 24 hours. The relative rate of deblocking was estimated from the cyan optical density that was quantified with an X-Rite reflection densitometer against a white background; a higher density of methylene blue indicates a higher deblocking conversion. After the deblocking period, the colorized discs were placed 2" from a bank of 40 W cool white fluorescent bulbs for 9 days, after which the cyan optical density was recorded; a higher density indicates higher retained methylene blue dye after the light exposure period, and thus better photostability. The following table shows that the deblocking rate is increased with higher levels of the alcohol containing monomer, SR495, and that photostability (resistance to light fading), is best with lower levels of SR495.

|  |  | Cyan Density (X-Rite) | |
| --- | --- | --- | --- |
| Formulation | % SR495 | 24 hrs 60° C. | 9 days Lights |
| I | 39 | 2.02 | 2.43 |
| II | 52 | 2.35 | 1.36 |
| III | 65 | 2.78 | 1.05 |

Bonding agents prepared with alkoxylated monomers have shown similar effects: increasing levels of Sartomer monomers SR502 (ethoxylated-9 trimethylol triacrylate) and CD501 (propoxylated-6 trimethylol triacrylate) result in increasingly poor photostability of TIPSOC-LMB derived methylene blue even in the presense of polyhydroxystyrenes.

An additional benefit of a polymeric light stabilizer is that a higher concentration of photostabilizer may be incorporated into the adhesive mixture with the upper limit to be found only as a result of high viscosity. Usable adhesives with concentrations of PHS as high as 25% by wt have been formulated; conventional monomeric phenolic organic compounds tend to form crystals which have been found to limit their solubility and thus their utility in active adhesive formulations.

A polymeric phenol made by the acid catalyzed addition of hydroxyphenyl carbinol, known as PHS-B, available from ChemFirst Electronic Materials L.P, has also been found to be very effective as a photostabilizer in these systems. Copolymers of 4-hydroxystyrene such as with styrene and butyl acrylate also show photostabilization effects in bonding resins; many copolymers would be expected to be effective here.

The photostability of azine dyes other than methylene blue is also improved with the addition of polyhydroxystyrene polymers.

EXAMPLE B

This example incorporates the use of a photostabilizer (polyhydroxystyrene) to prevent photobleaching of the oxidized disc. Excessive photobleaching of the methylene blue chromophore would lead to defeat of the limited play mechanism and result in a playable disc after exposure to a strong light source.

This example also incorporates the use of a reducing agent which results in an increase in the play time. The 4% level of stannous ethylhexanoate in this formulation provides a disc with play time of about 24 hours, whereas discs made using this formulation without added reducing agent provide a play time of about 8 hours.

| Component: | Wt. grams | Final Wt % |
| --- | --- | --- |
| Part A: | | |
| Sartomer SR440 | 32.50 | 10.08% |
| Sartomer SR238 | 65.00 | 20.16% |

-continued

| Component: | Wt. grams | Final Wt % |
|---|---|---|
| Sartomer SR495 | 97.50 | 30.24% |
| PHS8EO1 | 39.00 | 12.09% |
| Tinuvin 292 | 0.75 | 0.23% |
| Irgacure 819 | 5.20 | 1.61% |
| Part B: | | |
| Sartomer SR339 | 65.00 | 20.16% |
| TIPSOC-LMB | 4.50 | 1.40% |
| Stannous 2-Ethylhexanoate | 13.00 | 4.03% |

Part A was prepared by first combining the Sartomer monomers SR440, SR495 and SR231 (Sartomer Company, 502 Thomas Jones Way, Exton, Pa. 19341), followed by the dissolution of the polyhydroxystyrene (PHS-8EO1; Triquest, LP. 14785 Preston Road, Dallas, Tex. 75254-9123) with stirring and slight warming to 60° C. With continued stirring, the Tinuvin 292 (Ciba Specialty Chemcals, 540 White Plains Road, Tarrytown, N.Y. 10591-9005) was then added, followed by the Irgacure 819 (Ciba Specialty Chemcals, 540 White Plains Road, Tarrytown, N.Y. 10591-9005). The mixture was stirred in the dark until homogeneous. Part A is very stable and may be stored in the dark at about room temperature for several months before use.

Part B was prepared by dissolving TIPSOC-LMB in Sartomer SR339 under a nitrogen atmosphere with slight warming to 50° C. After cooling, the stannous ethylhexanoate (Sigma-Aldrich) was added and the solution was briefly stirred until homogeneous. Part B has limited stability and should be used within 8 hours.

The full active adhesive was then prepared by the addition of Part B to Part A followed by vigorous mixing at room temperature in the dark. The adhesive was used within four hours of mixing.

Additionally, photostability can be improved by adding resorcinol derivatives such as 4-hexylresorcinol or 4-cholorresorcinol Photostability may be further improved by increasing the TIPSOC concentration applied to the disc.

Monomer Selection

The monomers in the above examples were selected for their contribution to the following properties:

Solvency

The monomers of the present invention provide good ability to keep all the components in solution and free from particulate matter both during storage and during mixing of Parts A and B.

Viscosity

Because the polymeric nature of the preferred photostabilizer (PHS) tends to result in high mixture viscosities of the uncured resins, most monomers were selected for their low viscosity attributes in each functional group. Low viscosity of the uncured resin helps provide good flow characteristics during the spreading and spinning of the bonding agent between the two halves of the DVD during assembly.

Surface Tension

Spreading of the uncured bonding agent between the disc halves during manufacture is also facilitated in bonding agents that have lower surface tension.

Deblocking Rate

TIPSOC groups are deblocked with materials that are common to hydrolysis reactions; that is, water and alcohols with catalysis by bases and acids. The goal of the deblocking rate is to form sufficient LMB within one week at room temperature in the cured packaged disc.

Extended Playtime Resulting from Added Reducing Agents

Cured bonding agents that rely on stannous 2-ethylhexanoate to extend the useful playtime have been found to exhibit longer playtimes when higher levels of hydrophilic monomers are used. In some disc systems, this varies from 10 hours in cured discs without SR495 up to 24 hours in discs with 40% SR495.

Bond Strength

Multifunctional acrylates are used to provide crosslink density which contribute to the firmness and strength of the cured bonding resin. This, along with adhesion, helps maintain the alignment and physical dimensions of the DVD disc.

Photostability

Photostabilization of azine dyes occurs in part when the highly polar ionic azine dyes are formed in mediums of decreasing polarity with increasing levels of PHS.

The monomers from the above examples include:

SR495:

The polarity of the monomer blend contributes to the photostabilization by PHS of the resultant azine dyes. In the above examples, low levels of SR495, the alcohol containing caprolactone acrylate, result in better photostability of the expired disc, but those low levels of hydroxyl groups have an adverse effect on the deblocking rate of TIPSOC-LMB in the intially formed disc. Thus, the optimum level of the alcohol containing moiety is determined by the balance of these two effects, photostability and deblocking rate, and for the above examples is about 30% caprolactone acrylate.

Alternate high polarity monomers that increase deblocking rates have a similar adverse effect upon photostability; these include ethylene and propylene oxide derivatives and other monomers that contain polyether moieties. Similar effects were also seen with N-vinylpyrrolidone. These, and other hydrophilic acrylates may have advantage in other azine dye containing bonding agents assuming a proper balancing of properties.

Alternate hydroxyl containing monomers also include, but are not limited to hydroxyethyl acrylate, hydroxypropyl acrylate, hydroxybutyl acrylate, diethylene glycol monoacrylate and methacrylates as may be appropriate according to availability, toxicity and handling.

SR238, Hexanediol Diacrylate

This multifunctional acrylate contributes to crosslink density, which contributes to the strength of the cured adhesive. SR238 also contributes strongly to low viscosity of the uncured mixture and to the hydrophobic character of the cured resin. Other multifunctional acrylates that would also be expected to provide good results, assuming rebalancing of properties as described above, include trimethylolpropane triacrylate (SR351), and 1,3- and 1,4-butanediol diacrylates (SR212 and SR213), pentaerythritol triacrylate (SR444) pentaerythritol tetraacrylate (SR295), dipentaerythritol tetracrylate (SR355) and dipentaerythritol pentaacrylate (SR399). Alkoxylated multifuntional monomers may also be used with the appropriate balancing of properties. Oligimeric monomers such as epoxy and urethane acrylates, which typically are higher in viscosity than the materials described in this disclosure, may have advantage in some systems.

SR440, Isooctyl Acrylate

The incorporation of isooctyl acrylate (SR440) and also isodecyl acrylate (SR395), which are low surface tension materials (28 and 28.6 dynes/cm, respectively), has been observed to reduce the amount of incorporated air bubbles during manufacture and thus provides a higher disc yield. SR440 was found to be preferred over SR395 because of its greater range of solvency for PHS in combination with the other monomers. These monomers also contribute to low viscosity, low Tg, and low polarity. Many other alkyl acrylates would be expected to have a similar effect.

SR339, Phenoxyethyl Acrylate

This aromatic monomer is used as the main Part B monomer as it provides good solvency for both TIPSOC-LMB and the inadvertently formed methylene blue. It has been found that small amounts of TIPSOC-LMB deblocking do not effect the functioning of the resultant discs. Less polar monomers force the methylene blue to separate as crystals which require filtration to prevent disc defects. Another benefit of SR339 is that it provides a solution polarity that easily mixes with the PHS containing Part A without causing precipitation or other adverse mixing phenomena. One adverse effect of SR339 is a lowering of photostability, but the system may be rebalanced with a higher PHS level or a lower SR495 level.

Additional Deblocking Mechanisms

Carbamates can be used as protective groups for amines. Carbamates can be removed (de-blocked) by a variety of methods. These methods include, for example, acid and base hydrolysis, hydrogenolysis, β-eliminations with base, chemical reductions, electrolysis, thermolysis and photolysis. (See T. W. Greene and P. G. M. Wuts, *Protective Groups in Organic Synthesis*, 3$^{rd}$ Edition, John Wiley & Sons, pp 503–550, 1999 and references therein.)

Moreover, de-blocking mechanisms may also release various reagents which are useful for or aid in the generation of the colorless leuco-dye or the oxidized colored dye. For example, Patent # JP2000343837A, herein incorporated by reference in its entirety, uses thermal release of an acid to catalyze the de-blocking of t-BOC-LMB. Photoacid generators can also be used in a similar manner. The photorelease of radicals can be used to oxidize leuco-dyes(see for example U.S. Pat. No. 3,445,234 herein incorporated by reference in its entirety). Also, the thermal release of amines via hydrolysis of carbamates are also known, and include, for example, U.S. Pat. No. 6,015,771, hydrolysis incorporated by reference in its entirety.

A. Thermolysis

U.S. Pat. No. 4,602,263 and U.S. Pat. No. 4,826,976, both herein incorporated by reference in their entirety, teach the use of the thermally unstable carbamate moiety to protect dyes.

B. Photolysis

Photochemically labile protective groups are known. See, for example, V. N. R. Pillai, *Synthesis*, 1 (1980); Leuco methylene blue color formers with UV light including t-BOC (*J Photopolymer Science and Technology*, 14, 245–250 (2001); and Japanese Patent No. JP06032940, herein incorporated by reference, which uses leucomethylene blue carbamates for measuring the quantity of UV radiation.

Additional photolabile protecting groups include, for example, those described in the following references and the references incorporated therein. Tetrahedron Letters, No. 12, pp 1029–1030, 1979; Proc. Natl. Acad. Sci. USA, Vol 96, pp 1193–1200, February 1999; Tetrahedron Letters, 40, pp 1441–1444, 1999; and Synthesis, pp 1–26, January 1980. The following carbamates can be cleaved by photolysis: m-Nitrophenyl carbamate, 3,5-Dimethoxybenzyl carbamate, o-nitrophenyl carbamate, 2-(2-nitrophenyl)ethyl carbamate, 4-methoxyphenacyl carbamate, and 3,4-dimethoxy-6-nitrobenzyl carbamate.

C. Electrolysis

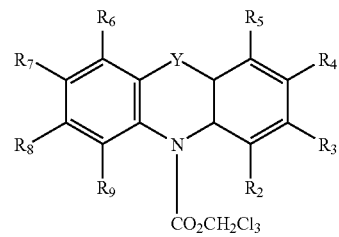

Examples include those materials described in the following references and the references listed therein:

1. L. Van Hijfte and R. D. Little, *J. Org. Chem.*, 50, 3940 (1985)
2. M. F. Semmelhack and G. E. Heinsohn, *J. Am. Chem. Soc.*, 94, 5139 (1972)
3. V. G. Mairianovsky, *Angew. Chem. Int. Ed. Engl.*, 15, 281 (1976)

D. β-Eliminations/Assisted β-Eliminations

One aspect of the present invention provides compounds of Formula (I):

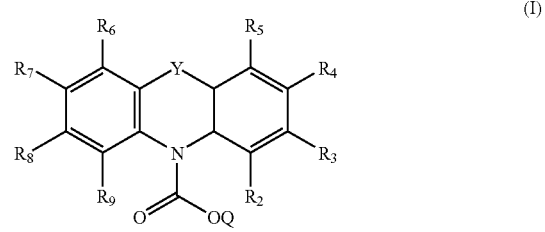

(I)

Q is any group capable of undergoing acid or base hydrolysis. Q can be removed under the appropriate conditions, which then causes the decarboxylation of the free carbamate group. Q can also be a group which ring closes on the carbonyl to eliminate the blocking group to furnish the leuco dye. The leuco dye is thereby unblocked, which if formed in the presence of oxygen, undergoes oxidation to the colored form of the dye. Representative groups for Q can be, but are not limited to $C_1$–$C_6$ alkyl, $C_1$–$C_6$ alkoxy, —$CH_2CH_2X$, aryl, substituted aryl, benzyl, substituted benzyl, and $SiR_{14}R_{15}R_{16}$, wherein X is either a leaving group capable of undergoing an E1 or E2 elimination reaction (β-eliminiation) or a moiety which can act as a nucleophile capable of ring closing;

$R_{14}$, $R_{15}$ and $R_{16}$ each is independently selected from hydrogen, unsubstituted $C_1$–$C_6$ alkyl, substituted $C_1$–$C_6$ alkyl, unsubstituted $C_1$–$C_6$ alkoxy, substituted $C_1$–$C_6$ alkoxy, benzyl and aryl groups. See, for example, T. W. Greene and P. G. M. Wuts, *Protective Groups in Organic Synthesis*, 3$^{rd}$ Edition, John Wiley & Sons, pp 540–2, 1999 and references therein.

Accordingly, a second aspect of the present invention provides compounds of Formula

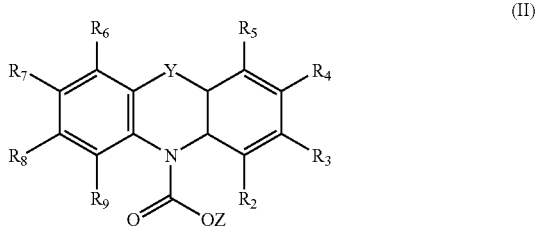

(II)

Z is any group capable of undergoing a β-elimination reaction. It has been disclosed that, in general, nitrogens protected by carbamoyl moieties that have attached to the corresponding carbamoyl oxygen a group capable of undergoing a β-elimination reaction will be deblocked under mildly basic conditions. This structure may be represented by Formula (III):

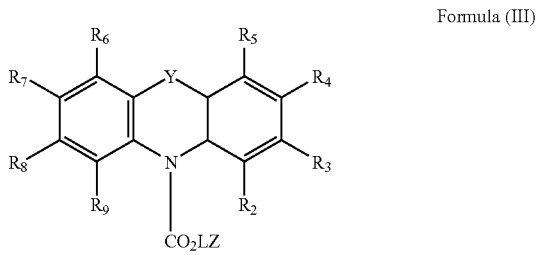

Formula (III)

Where Z is a substituent (carbanion-stabilizing group) capable of activating an adjacent moiety, L (Z itself call represent a protected group that must first be activated in order to assist in the β-elimination. See, for example, T. W. Greene and P. G. M. Wuts, *Protective Groups in Organic Synthesis*, 3$^{rd}$ Edition, John Wiley & Sons, pp 540–545, 1999 and references therein, that is capable of undergoing a β-elimination reaction. Where "dye" when taken with a carbamoyl moiety is a colorless precursor of the dye ("dye-precursor"), said Z-L- being substituted on the dye precursor such that the precursor is maintained in its colorless form, at least until the β-elimination reaction is initiated.

β-elimination reactions are well known in the art and represent base promoted 1, 2-elimination reactions. The release of a leaving group in this reaction (-Carbamoyl-Dye in formula (III) above) can be greatly accelerated when a carbanion-stabilizing group Z, is placed β to the leaving group. The choice of stabilizing group Z determines the rate at which the leaving group, Carbamoyl-Dye, is released. Any moiety that undergoes β-elimination may be employed as Z-L in formula (XI) above, provided that the elimination rate for the moiety provides the dye at a useful rate in a given color generating system. The rate constants for various leaving groups in elimination reactions of β-substituted sulphones, β-substituted phenyl ketones and β-substituted esters have been reported by Charles J. M. Stirling, et al, *J. Chem. Soc.* (B), 672–684 (1970); Charles J. M. Stirling et al, *J. Chem. Soc. Chem. Commun.*, 941 (1975); and Charles J. M. Stirling, *Acc. Chem. Res.* 12, 198–203 (1979). Examples of some leaving groups from a carbon system include —SMe; —SPh; —SePh; —OPh; —OMe; —P(O)(OEt)$_2$; —NHTs; —C(Me)$_2$ NO$_2$; —N(Me)Ts; —N(Me)Ac; —N(Ph)Ac; —N(Ph)Ts; —N(Ph)CO$_2$CH$_2$ Ph and —N(Me) CO$_2$Ph wherein Me, Et, Ph, Ac and Ts represent methyl, ethyl, phenyl, acetyl and tosyl, respectively. In particular, the carbamoyloxy leaving group in conjunction with sulfones has been reported by Kader, A. T. and Stirling, C. J. M., *J. Chem. Soc. Chem. Commun.*, 363, (1962).

A variety of amides are used in the art to protect amine functional groups (Greene pp. 550–564). Simple aides are generally very stable to acid or basic hydrolysis. However, the lability of the haloacetyl derivatives to mild acid hydrolysis makes the use of this moiety more practical for our application. In particular, the trifluoroacetyl group may be particularly advantagous (R. S. Goody and R. T. Walker, *Tetrahedron Lett.*, 289 (1967) as well as substituents that contain a neighboring hydroxyl group that can participate in an intramolecular hydrolysis (E. R. Kroft, P. Dorff, and R. Kullinig, *J. Org. Chem.*, 54, 2936 (1989). Another useful approach makes use of amides that are cleaved by intramolecular cyclization after activation (by reduction, photolysis, hydrolysis, silyl group cleavage). The concept of assisted cleavage is generalized below (see, for example, T. W. Greene et al. p. 561). As an example, one might have an alcohol group that is protected in the form of an ester which following hydrolysis induces deprotection by intramolecular addition to the amide carbonyl.

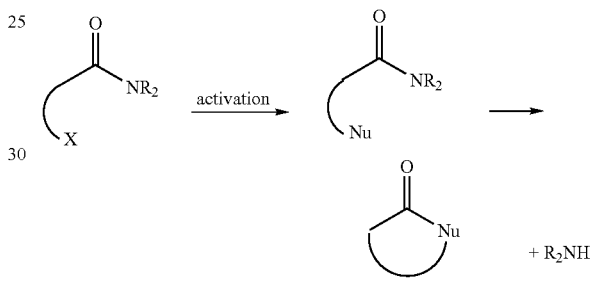

In this Scheme R$_2$NH would represent a leuco dye available for dye formation.

II. Novel Generation of Dyes

The interfering layer of the present invention that renders the disc unplayable by inhibiting the reading of the data does not need to be derived directly from blocked precursors of oxygen sensitive leuco dyes such as those disclosed above.

1. One embodiment could use blocked/protected intermediates that when activated (by any of the methods described above) would result in the formation of the leuco-dye "in-situ" in a stepwise manner. The colorless leuco-dye would then be oxidized in the presence of oxygen to the highly colored dye. The following scheme resulting in the blue dye, indigo, is illustrative of the embodiment.

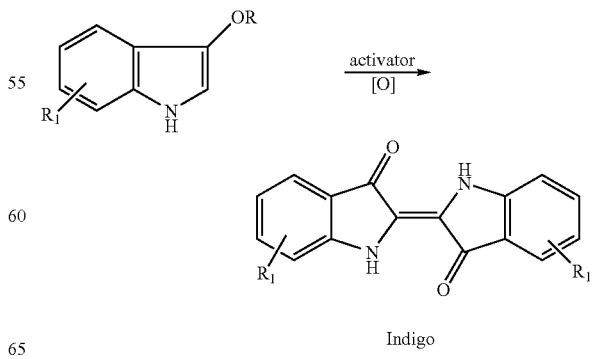

Indigo

2. Oxidative coupling of one or more primary intermediates with one another or with one or more secondary intermediates can lead to highly colored compounds. These coloring systems are familar to those in the photographic/imaging industries. The coupling of a color developer with a dye forming coupler moiety substituted at the coupling carbon with a thermally, photolytically or hydrolytically removable leaving group is known in dye chemistry. These intermediates may be protected or blocked using methods known in the art and activated to de-blocked by any of the methods discussed above. The de-blocked intermediates are then free to interact in a color forming reaction.

E. Combinations of De-Blocking Method

Combinations of de-blocking can be applied either to an individual leuco-dye (see assisted β-eliminations), to mixtures of leuco-dyes where each incorporates a different de-blocking method, or to a mixture of a single leuco-dye that is protected with a variety of de-blocking groups (see, for example, Krieg-Kowald, US Patent Application Publication US Published Utility Patent Application No. 2002/0102499A1, Aug. 1, 2002 and herein incorporated by reference in its entirety).

It should be understood that combinations of any of the disclosed de-blocking mechanisms can be used to gain better control of the de-blocking kinetics, increase stability of the interfering layer towards bleaching or to satisfy other stability requirements related to the blocked dye (or leuco dye). For example, a combination of a basic hydrolysis and photolytic de-blocking can be used to give added protection against attempts to photobleach the oxidized dye (methylene blue) which is generated via the base assisted de-blocking reaction.

Preventing Expired Discs from Playing in Future Generation Players.

Future generations of optical discs and players are typically developed to offer increased performance for consumers and other users of the technology. For example, DVDs offer increased storage capacity compared to CDs, and the next generation of "blue laser" DVDs will offer improved capacity compared to today's DVDs. Subsequent generations of optical storage media, such as the "DVR" format currently under development, will have even greater capacity and performance.

Optical media players are typically engineered with the ability to play previous generations of discs. For example, while CD players employ a laser with a wavelength of 780 nanometers to read CDs, DVD players typically employ their reading laser with a wavelength of 650 nanometers to read CD discs. The next generation DVDs ("blue laser DVDs") is designed to be read with a laser with a wavelength of 450–460 nanometers; the "DVR" format will use lasers emitting around 405 nm. Future generation players are likely to be able to read current DVDs with their 450–460 nanometer or 405 nanometer lasers.

Dyes used to inhibit the reading laser in current optical disc players are typically designed to interfere with the reading laser employed by these players; such dyes, however, may not interfere with the reading laser future players, which is likely to have a shorter wavelength. The implication is that expired discs, even though they may not play in the current generation of players, they may become playable when future generation players become available. Dyes used to inhibit the reading laser in current DVD players are typically designed to interfere with a 650 nanometer reading laser; such dyes, however, may not interfere with a reading laser in the 450–460 nanometer rage. For example, methylene blue, which is one of the read inhibit dyes proposed in Smith et al, while strongly absorbent in the 650 nanometer wavelength, it is essentially transparent in the 450–460 nanometer range (see FIG. 19). The implication is that expired DVDs may play in blue laser DVD players.

Another embodiment of the present invention is an optical disc that will not play in future generation players, thus preventing an expired disc from becoming playable when future generation players (blue laser DVD players) become available. This can be accomplished by incorporating in the optical path of the disc a selectively interfering layer that will interfere with the reading laser of future generation players, and thus will inhibit reading of the disc in such players. Such a layer can be designed by incorporating a dye or pigment that does not interfere with the reading laser in a certain type of players, but does interfere with the reading laser in other types of players (or will change to become interfering in response to a predetermined stimulus). For example, Acridine Yellow [135-49-9], is essentially transparent at the 635–650 nanometer wavelength but strongly absorbs at the 450–460 and 405 nanometer wavelengths (absorption max in ethanol at 462 nm, molar absorptivity= 37,000 $M^{-1}cm^{-1}$). Alternatively 9,10-bis(phenylethynyl)anthracene [10075-85-1] also does not absorb at all in the 635–650 nanometer range, but is strongly absorbent in the 450–460 and 405 nanometer range (absorbance max 455 nm in cyclohexane, molar absorptivity 33,000 $M^{-1}cm^{-1}$). Other classes of dyes and pigments that can be used for blocking blue laser light (at either 450–460 or 405 nm) include aromatic hydrocarbons, azo dyes, cyanines, polymethines, carotinoids, hemicyanines, styryls, quinaldines, coumarins, di- and triarylmethines, anthraquinones, nitro and nitrosos. As mentioned above, methylene blue is essentially transparent at the 450–460 nanometer wavelengths, but strongly absorbs at the 635–650 nanometer range.

In one embodiment of the current invention, the selectively interfering layer is a dedicated layer in the optical path of the reading laser. In another embodiment, which is likely to be the preferred embodiment because it does not introduce an additional design element for the optical disc, the selectively interfering layer is combined with another element of the disc, such as the substrate or the reactive layer. For example, this could be accomplished by mixing an appropriate dye or pigment, such as Acidine Yellow [135-49-9] or 9,10-bis(phenylethynyl)anthracene [10075-85-1], with the polycarbonate or other polymer used to mold the substrate of the disc, or with the reactive layer in an expiring disc, such as the bonding layer in the special DVD-5 designs described earlier.

Optionally, the reactive material belongs to the class of dyes known as Fluoran dyes. A Fluoran dye can be blocked and/or protected and/or modified with a chemical moiety. Once unblocked the Fluoran dye, in response to a triggering stimulus and/or stimuli, would transition from a colorless form to black. Such a system would not require an additional dye or pigment to insure that the disc, once expired, does not play in media players of different wavelengths.

Use of Additional Mechanisms to Prevent Recovery of Data

Another embodiment of the present invention is combining the mechanism(s) that prevent reading of the optical disc by inhibiting the reading laser with additional mechanism(s) for preventing recovery of the information encoded in the data structures on the disc. These additional mechanism(s) can be designed with less accurate control of the timing of their activation than the mechanism(s) that work by inhibiting the reading laser. Thus it may be desirable to combine the mechanism that controls expiration of the optical disc by interfering with the residing laser with additional mechanism(s) that permanently prevent the recovery of the data on the optical disc. For example, a disc may become unplayable by transitioning a layer in the optical path from transparent to opaque in a controlled time period, for example approximately 24 hours after a predetermined stimulus, such as removing the disc from its packaging. In addition, a secondary mechanism could corrode the metal layer on the disc, such mechanism acting over a longer period of time, such as 1–2 weeks, and being triggered by the same or a different stimulus. Additional mechanisms may also be employed, such as an additive that degrades the polycarbonate material from which the disc is composed, which process can be triggered by the same stimulus (such as exposure to ambient air), or a different stimulus (such as the centrifugal forces generated when a disc is played in a CD or DVD player). Other triggering stimuli for these backup mechanisms can include various constituents of air, light, physical motion, and time from manufacturing or packaging. Many other mechanisms are possible.

One method of accomplishing this is to deposit a layer of metallic silver separated from the information bearing aluminum layer by a material incorporated for this purpose, or by an existing material, such as the bonding layer or one of the substrates of the optical disc. This silver layer can be above or below the aluminum layer, and if it is below (and thus in the optical path of the reading laser) it needs to be sufficiently transparent initially so that the reading laser can read the information on the aluminum layer.

In one embodiment of the invention, a DVD-9 disc is manufactured with a reactive bonding layer consisting of a material with appropriate dielectric properties, and with appropriate selection of metals for L0 and L1. For example, L0 can be made of silver and L1 can be made of aluminum.

When a silver layer and an aluminum layer are separated by an appropriate dielectric material, then upon exposure to oxygen the silver serves as a cathode, on which $O_2$ is reduced, and aluminum serves as an anode. Corrosion is fast only if a short develops between the silver and the aluminum layers. The development of the short results from the growth of a silver dendrite through the separating material. To grow the dendrite through the separating material it is desirable to use a material that has some ionic conductivity. Several likely separating materials consist of or contain polyacrylate. If the polyacrylate is slightly hydrolyzed, or if it is, for example, a 2-hydroxyethylacrylate copolymer, there will be some ionic conductivity. Preferred are co-polymers of poly(acrylonitrile), or of poly(4-vinylpyridine), or of poly(1-vinylimidazole). All of these should conduct silver, copper or thallium ions ($Ag^+$ $Cu+$ or $Tl+$). Thallium is less preferred due to its toxicity.

The chemical equations are as follows:
Silver is air-oxidized:

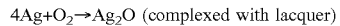
$4Ag+O_2 \rightarrow Ag_2O$ (complexed with lacquer)

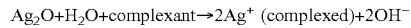
$Ag_2O+H_2O+complexant \rightarrow 2Ag^+$ (complexed)$+2OH^-$ $Ag^+$ is reduced by aluminum, which is oxidized (if $Ag^+$ is mobile in the lacquer, which is designed to conduct $Ag^+$)

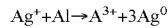
$Ag^+ + Al \rightarrow Al^{3+} + 3Ag^0$

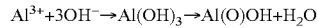
$Al^{3+} + 3OH^- \rightarrow Al(OH)_3 \rightarrow Al(O)OH + H_2O$

A silver dendrite starts growing from the aluminum to the silver. When the two layers are shorted, the "switch" between a battery's (Al) anode and (Ag) cathode is closed. Corrosion is rapid and catastrophic. One skilled in the art will recognize that other similar metals may be substituted for Al and Ag in this example.

Alternatively, one embodiment of the present invention takes advantage of technology employed in the photographic industry. This technology is used to remove the silver image following the development of the dye images in color photography. This is accomplished through a technique called "bleaching" where the silver image is oxidized to silver ion and then removed with a silver solvent (fixing). The list of possible oxidants is large and include, for example, the mechanism depicted below:

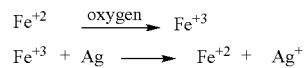

The ferrous ion is air oxidized to the ferric ion, which is capable of oxidizing the silver forming ferrous ion which in turn can then complete the cycle again. The silver ion is capable of migration, thereby compromising the integrity of the information. The redox reaction becomes more thermodynamically favorable depending on the chelator (counter ion) used to solublize the iron (EDTA, 8-hydroxquinoline, phenanthroline, acetoacetonate, ferrocene, etc.).

Additionally, there are a variety of compounds known in the photographic field that act as accelerators of the bleaching reaction. These include, for example, but not by way of limitation: polyoxyethylene polymers containing side chains with thioether groups, mercaptotriazoles, mercaptothiadiazoles, mercaptoimidazoles, mercaptotetrazoles, imidazoles, monothioglycerol, cystine, cysteine, cystamine, thiourea derivatives, thioamide compounds, aminoalkylene thiols, etc. Compounds known as anti-foggants have also been shown to act as bleach accelerators.

According to another overlapping embodiment of the present invention $Fe^{+2}$ is solubilized with a low potential chelator that is displaced after packaging with a high potential chelator following a de-blocking mechanism.

Optionally, hydroquinone-quinone redox chemistry can be used to accomplish the same thing as the ferrous salts. A blocked hydroquinone is de-blocked in the package and air oxidized to the quinone on exposure to air which in turn oxidizes the silver. This approach can also take advantage of bleaching accelerators.

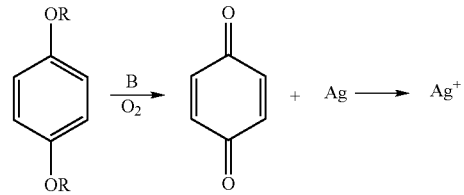

Alternatively, other ways of permanently corroding data layers via the reactive layer can be employed. For example, certain embodiments of this invention may have a bonding layer that promotes the corrosion of the reflective metal layer or may involve the diffusion of some substance from the bonding layer to the reflective layer(s). For example, the presence of halide ions has been observed to corrode thin silver layers and prevent reading of the DVD. Mechanisms could be envisioned to release or activate halide ions and thus inhibit reading of the data. In other embodiments, the additional mechanisms will not be part of the bonding material. For example, a precursor of a corrosive substance may be deposited adjacent to the metal layer. When oxygen or some other appropriate substance diffuses through the substrate and reaches the corrosive precursor, a reaction could be initiated that results in producing a corrosive substance that over a period of time permanently destroys the data structures on the disc. Alternatively, the material in the Substrate of the disc, such as polycarbonate, could be engineered so that it degrades over a period of time, thus making the disc unusable. Such substances and reactions are known to the skilled in the art.

Another composition that performs a similar function is one in which the substrate itself is modified over time. The modification of the substrate could cause it to change its optical qualities, thereby degrading the signal reaching the reader. These optical qualities could include its index of refraction or its transparency.

Moreover, the modification of the substrate could cause the underlying metal layer to change its optical properties, as described above. In this way, a time-sensitive substrate and/or lacquer could be combined with a reflective layer that becomes non-reflective.

The transparency of a polymer film can be changed by any of the following: reaction of the film with water; reaction of the film with oxygen; or crystallization of the polymer, meaning increased alignment of polymer molecules in the film.

As an example, a substrate could be chosen that is changed by components in air such as oxygen or water. For example, oxygen could oxidize the substrate, causing a change in its transparency or its index of refraction. Alternatively, the substrate could be designed to absorb water in the air, causing it to swell and change its optical properties. Another example is that the substrate could change its permeability to oxygen over time, thereby permitting the oxidation of the metallic layer. In the later case, the overall time sensitivity of the optical media could be a function of the properties of both the substrate and/or lacquer and the reflective layer.

The substrate or the metallic layer could also be made sensitive to specific wavelengths of light. Exposure to these wavelengths would cause a change in the optical qualities of the layer, thereby degrading the signal reaching the reader. Examples include photodepolymerization of the substrate; photogeneration of acid or base; photogeneration of singlet oxygen; and unzipping of the polymers (e.g. fissure of cross linking hydrogen bonds). Incorporation of light-activated catalysts into the substrate or the metallic layer can assist in this process.

The following paragraph should be eliminated. You misinterpreted my use of the indigo dyes. I had two possible uses of indigo dyes. 1) they were an example of the possible generation of leuco-dyes in-situ meaning the leuco form of the dye is actually synthesized (through a deblocking mechanism) in the disk in an unprotected form 2) since they are highly insoluble when formed.

Accordingly, the present invention has been described at some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

Equivalents

As will be apparent to those skilled in the art to which the invention pertains, the present invention may be embodied in forms other than those specifically disclosed above without departing from the spirit or essential characteristics of the invention. The particular embodiments of the invention described above are, therefore, to be considered as illustrative and not restrictive. The scope of the invention is as set forth in the appended claims rather than being limited to the examples contained in the foregoing description.

What is claimed as new and desired to be protected by letters patent is set forth in the following claims.

What is claimed is:

1. A compound of formula I:

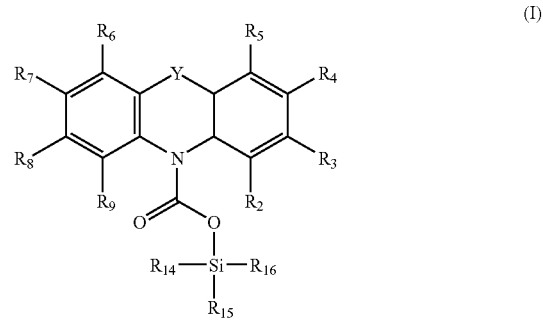

wherein

Y is O, S, Se, $CR_{17}R_{18}$, $NR_{13}$, wherein $R_{13}$, $R_{17}$, $R_{18}$ is each independently selected from hydrogen, $C_1$–$C_3$ alkyl and substituted aryl groups and unsubstituted aryl groups;

$R_2$, $R_5$, $R_6$, and $R_9$ each is independently selected from hydrogen, halogen, $C_1$–$C_6$ alkyl, $C_1$–$C_6$ alkoxy, aryl, nitro, azo and fused aromatic groups;

$R_3$, $R_4$ $R_7$, and $R_8$ each is independently selected from $NR_{10}R_{11}$, $OR_{12}$, hydrogen, alkyl, aryl, azo, and fused aromatic groups; and $R_{10}$, $R_{11}$, $R_{12}$, $R_{14}$, $R_{15}$ and $R_{16}$ each is independently selected from hydrogen, unsubstituted $C_1C_6$ alkyl, substituted $C_1$–$C_6$ alkyl, unsubstituted $C_1$–$C_6$ alkoxy, and substituted $C_1$–$C_6$ alkoxy, benzyl or aryl groups.

2. The compound of claim 1, wherein Y is S.

3. The compound of claim 1, wherein $R_4$ is selected from $NR_{10}R_{11}$ and $OR_{12}$.

4. The compound of claim 1, wherein $R_7$ is selected from $NR_{10}R_{11}$ and $OR_{12}$.

5. The compound of claim 1, wherein Y is S; $R_4$ and $R_7$ is $NR_{10}R_{11}$; and $R_2$, $R_3$, $R_5$, $R_6R_8$, and $R_9$ each is independently selected from hydrogen, halogen, alkyl, aryl, nitro, and fused aromatic groups.

6. The compound of claim 5, wherein $R_{14}$, $R_{15}$ and $R_{16}$ is each independently selected from hydrogen, unsubstituted $C_1$–$C_6$ alkyl, substituted $C_1$–$C_6$ alkyl, unsubstituted $C_1$–$C_6$ alkoxy, and substituted $C_1$–$C_6$ alkoxy.

7. The compound of claim 6, wherein $R_{14}$, $R_{15}$ and $R_{16}$ is each independently selected from methyl, ethyl, n-propyl and isopropyl.

8. The compound of claim 7, wherein $R_{14}$, $R_{15}$ and $R_{16}$ is isopropyl.

9. The compound of claim 8, wherein $R_2$, $R_3$, $R_5$, $R_6$, $R_8$, and $R_9$ each is hydrogen; $R_{10}$ and $R_{11}$ each is methyl.

10. The compound of claim 1, wherein Y is O.

11. The compound of claim 10, wherein $R_4$ is selected from $NR_{10}R_{11}$ and $OR_{12}$.

12. The compound of claim 10, wherein $R_7$ is selected from $NR_{10}R_{11}$; and $OR_{12}$.

13. The compound of claim 10, wherein Y is O; $R_4$ and $R_7$ is $NR_{10}R_{11}$; and $R_2$, $R_3$, $R_5$, $R_6$, $R_8$, and $R_9$ each is independently selected from hydrogen, halogen, alkyl, aryl, nitro, and fused aromatic groups.

14. The compound of claim 13, wherein $R_{14}$, $R_{15}$ and $R_{16}$ is each independently selected from hydrogen, unsubstituted $C_1$–$C_6$ alkyl, substituted $C_1$–$C_6$ alkyl, unsubstituted $C_1$–$C_6$ alkoxy, and substituted $C_1$–$C_6$ alkoxy.

15. The compound of claim 14, wherein $R_{14}$, $R_{15}$ and $R_{16}$ is each independently selected from methyl, ethyl, n-propyl and isopropyl.

16. The compound of claim 15, wherein $R_{14}$, $R_{15}$ and $R_{16}$ is isopropyl.

17. The compound of claim 16, wherein $R_2$, $R_3$, $R_5$, $R_6$, $R_8$, and $R_9$ each is hydrogen; $R_{10}$ and $R_{11}$ each is methyl.

18. The compound of claim 1, wherein Y is N.

19. The compound of claim 18, wherein $R_4$ is selected from $NR_{10}R_{11}$ and $OR_{12}$.

20. The compound of claim 18, wherein $R_7$ is selected from $NR_{10}R_{11}$ and $OR_{12}$.

21. The compound of claim 18, wherein Y is N; $R_4$ and $R_7$ is $NR_{10}R_{11}$; and $R_2$, $R_3$, $R_5$, $R_6$, $R_8$, and $R_9$ each is independently selected from hydrogen, halogen, alkyl, aryl, nitro, and fused aromatic groups.

22. The compound of claim 21, wherein $R_{14}$, $R_{15}$ and $R_{16}$ is each independently selected from hydrogen, unsubstituted $C_1$–$C_6$ alkyl, substituted $C_1$–$C_6$ alkyl, unsubstituted $C_1$–$C_6$ alkoxy, and substituted $C_1$–$C_6$ alkoxy.

23. The compound of claim 22, wherein $R_{14}$, $R_{15}$ and $R_{16}$ is each independently selected from methyl, ethyl, n-propyl and isopropyl.

24. The compound of claim 23, wherein $R_{14}$, $R_{15}$ and $R_{16}$ is isopropyl.

25. The compound of claim 24, wherein $R_2$, $R_3$, $R_5$, $R_6$, $R_8$, and $R_9$ each is hydrogen; $R_{10}$ and $R_{11}$ each is methyl.

26. A compound of formula II:

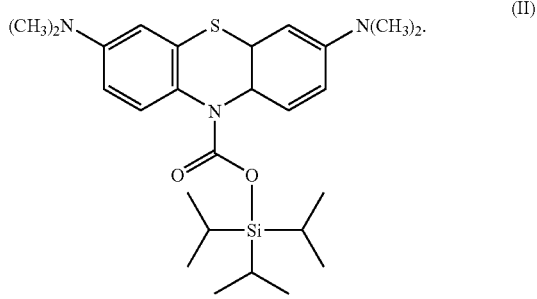

27. A compound of formula III:

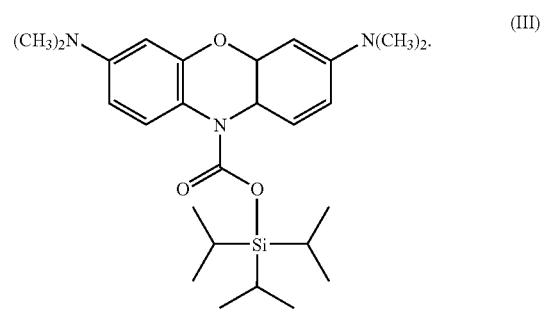

28. A compound of formula IV:

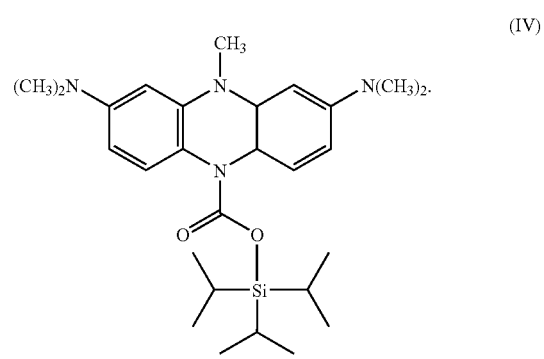

29. An optical media comprising:
a first substrate and a second substrate, wherein at least one of said first substrate and said second substrate has information encoding features;
a bonding layer between said first and said second substrates;
wherein said bonding layer transforms from a transparent state to an opaque state and comprises;
a carrier material, wherein said carrier material comprises at least one of thermoplastic acrylic polymers, polyester resins, epoxy resins, polythiolenes, ultraviolet cured organic resins, polyurethanes, thermosettable acrylic polymers, alkyds, vinyl resins, and combinations thereof;
a reactive material, wherein said reactive material comprises a reduced form of at least one dye selected from azines, oxazines, thiazines, leuco-azines, quinoneimines, indamines, indophenols, indoanilines, anthraquinones, acridines, diarylmethane, triarylmethane and combinations thereof; and
a photostabilizing material, wherein said photostabilizing material comprises at least one polymeric phenol material.

* * * * *